(12) United States Patent
Bunnage et al.

(10) Patent No.: US 7,056,934 B2
(45) Date of Patent: Jun. 6, 2006

(54) NICOTINAMIDE DERIVATIVES USEFUL AS PDE4 INHIBITORS

(75) Inventors: Mark Edward Bunnage, Sandwich (GB); John Paul Mathias, Sandwich (GB)

(73) Assignee: Pfizer Inc, New York, NY (US)

( * ) Notice: Subject to any disclaimer, the term of this patent is extended or adjusted under 35 U.S.C. 154(b) by 18 days.

(21) Appl. No.: 10/896,071

(22) Filed: Jul. 20, 2004

(65) Prior Publication Data

US 2005/0038033 A1 Feb. 17, 2005

Related U.S. Application Data

(60) Provisional application No. 60/497,079, filed on Aug. 22, 2003.

(30) Foreign Application Priority Data

Jul. 25, 2003 (GB) ................................. 0317484.4

(51) Int. Cl.
*C07D 401/02* (2006.01)
*C07D 213/02* (2006.01)
*A61K 31/44* (2006.01)

(52) U.S. Cl. ................... 514/341; 514/350; 546/272.7; 546/275.4; 546/298

(58) Field of Classification Search ................ 546/298, 546/300, 301, 272.7, 275.4; 514/345, 350, 514/351, 341
See application file for complete search history.

(56) References Cited

U.S. PATENT DOCUMENTS

| | | | |
|---|---|---|---|
| 6,380,218 B1 | 4/2002 | Marfat et al. | 514/326 |
| 6,559,168 B1 | 5/2003 | Marfat et al. | 514/338 |
| 6,649,633 B1 | 11/2003 | Chambers et al. | 514/337 |
| 6,740,655 B1 | 5/2004 | Magee et al. | 514/255.02 |
| 2002/0111495 A1 | 8/2002 | Magee et al. | 546/291 |

FOREIGN PATENT DOCUMENTS

| | | |
|---|---|---|
| WO | WO9845268 | 10/1998 |
| WO | WO0157025 | 8/2001 |
| WO | WO0157036 | 8/2001 |
| WO | WO0260896 | 8/2002 |
| WO | WO0368235 | 8/2003 |

OTHER PUBLICATIONS

Torphy et al., "Phosphodiesterase IV Inhibitors as Therapy for Eosinophil-induced Lung Injury in Asthma", Environmental Health Perspectives, 1994, 102 Suppl. 10, p. 79-84.
Duplantier et al., "Biarylcarboxylic Acids and -amides: Inhibition of Phosphodiesterase Type IV verses [$^3$H]Rolipram Binding Activity and Their Relationship to Emetic Behavior in the Ferret", J. Med. Chem., 1996, 39, p. 120-125.

Schneider et al., "Discriminative Stimulus Properties of the Stereoisomers of the Phosphodiesterase Inhibitor Rolipram", Pharmacology Biochemistry Behavior, 1995, 50, p. 211-217.
Banner and Page, "Acute versus chronic administration of phosphodiesterase inhibitors on allergen-induced pulmonary cell influx in sensitized guinea-pigs", British Journal of Pharmacology, 1995, 114, p. 93-98.
Barnette et al., "The ability of phosphodiesterase IV inhibitors to suppress superoxide production in guinea pig eosinophils is correlated with inhibition of phosphodiesterase IV catalytic activity", J. Pharmacol. Exp. Ther., 1995, 273, p. 674-679.
Wright et al., "Differential in vivo and in vitro bronchorelaxant activities of CP-80,633, a selective phosphodiesterase 4 inhibitor", Can. J. Physiol. Pharmacol., 1997, 75, p. 1001-1008.
Manabe et al., "Anti-inflammantory and bronchodilator properties of KF19514, a phosphodiesterase 4 and 1 inhibitor", European Journal of Pharmacology, 1997, 332, p. 97-107.
Ukita et al., "Novel Potent, and Selective Phosphodiesterase-4 Inhibitors as Antiasthmatic Agents: Synthesis and Biological Activities of a Series of 1-Pyridylnaphthalene Derivatives", J. of Med. Chem., 1999, 42, p. 1088-1099.

(Continued)

*Primary Examiner*—Zinna Northington Davis
(74) *Attorney, Agent, or Firm*—Gregg C. Benson; Robert T. Ronau

(57) ABSTRACT

This invention relates to nicotinamide derivatives of general formula (I):

in which $R^1$, $R^2$ and $R^3$ have the meanings defined herein, and to processes for the preparation of, intermediates used in the preparation of, compositions containing and the uses of such derivatives.

26 Claims, No Drawings

NICOTINAMIDE DERIVATIVES USEFUL AS PDE4 INHIBITORS

This invention relates to nicotinamide derivatives of general formula (I):

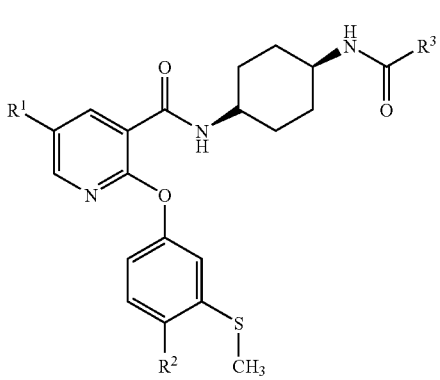

in which $R^1$, $R^2$ and $R^3$ have the meanings indicated below, and to processes for the preparation of, intermediates used in the preparation of, compositions containing and the uses of such derivatives.

The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. A total of more than fifteen gene products is included within this class, and further diversity results from differential splicing and post-translational processing of those gene products. The present invention is primarily concerned with the four gene products of the fourth family of PDEs, i.e., PDE4A, PDE4B, PDE4C, and PDE4D. These enzymes are collectively referred to as being isoforms or subtypes of the PDE4 isozyme family.

The PDE4s are characterized by selective, high affinity hydrolytic degradation of the second messenger cyclic nucleotide, adenosine 3',5'-cyclic monophosphate (cAMP), and by sensitivity to inhibition by rolipram. A number of selective inhibitors of the PDE4s have been discovered in recent years, and beneficial pharmacological effects resulting from that inhibition have been shown in a variety of disease models (see, e.g., Torphy et al., *Environ. Health Perspect.*, 1994, 102 Suppl. 10, p. 79–84; Duplantier et al., *J. Med. Chem.*, 1996, 39, p. 120–125; Schneider et al., *Pharmacol. Biochem. Behav.*, 1995, 50, p. 211–217; Banner and Page, *Br. J. Pharmacol.*, 1995, 114, p. 93–98; Barnette et al., *J. Pharmacol. Exp. Ther.*, 1995, 273, p. 674–679; Wright et al., *Can. J. Physiol. Pharmacol.*, 1997, 75, p. 1001–1008; Manabe et al., *Eur. J. Pharmacol.*, 1997, 332, p. 97–107 and Ukita et al., *J. Med. Chem.*, 1999, 42, p. 1088–1099). Accordingly, there continues to be considerable interest in the art with regard to the discovery of further selective inhibitors of PDE4s.

Successful results have already been obtained in the art with the discovery and development of selective PDE4 inhibitors. In vivo, PDE4 inhibitors reduce the influx of eosinophils to the lungs of allergen-challenged animals while also reducing the bronchoconstriction and elevated bronchial responsiveness occurring after allergen challenge. PDE4 inhibitors also suppress the activity of immune cells (including CD4+ T-lymphocytes, monocytes, mast cells, and basophils), reduce pulmonary edema, inhibit excitatory nonadrenergic noncholinergic neurotransmission (eNANC), potentiate inhibitory nonadrenergic noncholinergic neurotransmission (iNANC), reduce airway smooth muscle mitogenesis, and induce bronchodilation. PDE4 inhibitors also suppress the activity of a number of inflammatory cells associated with the pathophysiology of COPD, including monocytes/macrophages, CD4+ T-lymphocytes, eosinophils and neutrophils. PDE4 inhibitors also reduce vascular smooth muscle mitogenesis and potentially interfere with the ability of airway epithelial cells to generate pro-inflammatory mediators. Through the release of neutral proteases and acid hydrolases from their granules, and the generation of reactive oxygen species, neutrophils contribute to the tissue destruction associated with chronic inflammation, and are further implicated in the pathology of conditions such as emphysema. Therefore, PDE4 inhibitors are particularly useful for the treatment of a great number of inflammatory, respiratory and allergic diseases, disorders or conditions and for wounds and some of them are in clinical development mainly for treatment of asthma, COPD, bronchitis and emphysema.

The effects of PDE4 inhibitors on various inflammatory cell responses can be used as a basis for profiling and selecting inhibitors for further study. These effects include elevation of cAMP and inhibition of superoxide production, degranulation, chemotaxis, and tumor necrosis factor alpha (TNFa) release in eosinophils, neutrophils and monocytes.

Some nicotinamide derivatives having a PDE4 inhibitory activity have already been synthetized. For example, the patent application WO 98/45268 discloses nicotinamide derivatives having activity as selective inhibitors of PDE4D isozyme.

The patent applications WO 01/57036 and WO 03/068235 also disclose nicotinamide derivatives which are PDE4 inhibitors useful in the treatment of various inflammatory allergic and respiratory diseases and conditions.

However, there is still a huge need for additional PDE4 inhibitors that are good drug candidates. In particular, preferred compounds should bind potently to the PDE4 enzyme whilst showing little affinity for other receptors and enzymes. They should also possess favourable pharmacokinetic and metabolic activities, be non-toxic and demonstrate few side effects. Furthermore, it is also desirable that the ideal drug candidate will exist in a physical form that is stable and easily formulated.

The present invention therefore provides new nicotinamide derivatives of formula (I):

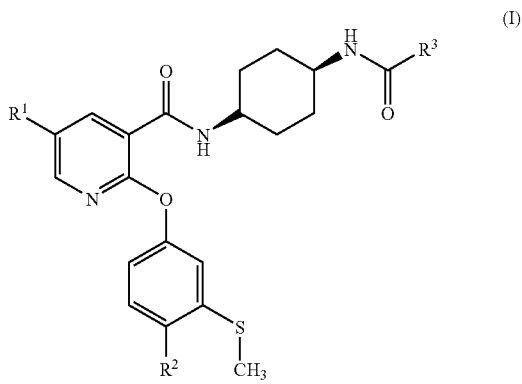

or pharmaceutically acceptable salts, solvates, polymorphs or prodrugs thereof wherein:
$R^1$ and $R^2$ are each independently selected from the group consisting of hydrogen, halo, and $(C_1-C_3)$alkyl;

and wherein $R^3$ is selected from a C-linked 5- or 6-membered heteroaryl containing 1, 2 or 3 nitrogen atoms wherein said heteroaryl is substituted by a hydroxy $(C_1-C_4)$alkyl group and is optionally further substituted by one or more groups selected from OH, halo, $(C_1-C_4)$ alkyl and $(C_1-C_4)$alkoxy, or a phenyl group substituted by a hydroxy$(C_1-C_4)$alkyl group or a hydroxy$(C_2-C_4)$alkoxy group and wherein said phenyl group is optionally further substituted by one or more groups selected from OH, $(C_1-C_4)$alkoxy, $(C_1-C_4)$alkyl and halo.

Preferably $R^1$ is H, F, Cl or methyl, more preferably $R^1$ is F, Cl or methyl.

Preferably $R^2$ is H or F, more preferably $R^2$ is H.

When $R^3$ is a C-linked 5- or 6-membered heteroaryl, preferably said heteroaryl contains 2 or 3 nitrogen atoms.

When $R^3$ is a C-linked 5- or 6-membered heteroaryl, more preferably it is a C-linked pyrazole or imidazole group.

When $R^3$ is a C-linked 5- or 6-membered heteroaryl, highly preferred are C-linked pyrazole or imidazole groups wherein one of the ring nitrogen atoms is substituted by a hydroxy$(C_2-C_3)$alkyl group and wherein the ring is optionally further substituted by one or more groups selected from $(C_1-C_4)$alkyl and $(C_1-C_4)$alkoxy.

When $R^3$ is a C-linked 5- or 6-membered heteroaryl, especially preferred are C-linked pyrazole or imidazole groups wherein one of the ring nitrogen atoms is substituted by a hydroxy$(C_2-C_3)$alkyl group and wherein the ring is optionally further substituted by one or more $(C_1-C_4)$alkyl groups.

Preferred substituents on one of the ring nitrogen atoms in said pyrazole or imidazole groups are hydroxyethyl and hydroxypropyl.

Preferred optional substitutents on said pyrazole or imidazole groups, wherein one of the ring nitrogen atoms is substituted by a group selected from hydroxyethyl and hydroxypropyl, are one or more groups selected from methyl, ethyl, n-propyl and isopropyl.

More preferred optional substitutents at the 5-position on said pyrazole or imidazole groups, wherein one of the ring nitrogen atoms is substituted by a group selected from hydroxyethyl and hydroxypropyl, are one or more groups selected from methyl, ethyl, n-propyl and isopropyl.

When $R^3$ is a phenyl group substituted by a hydroxy $(C_1-C_4)$alkyl group or a hydroxy$(C_2-C_4)$alkoxy group then preferably $R^3$ a phenyl group substituted by a hydroxymethyl or a hydroxyethoxy group and wherein said phenyl group is optionally further substituted by one or more groups selected from OH, methyl, ethyl, F and Cl.

When $R^3$ is a phenyl group substituted by a hydroxy $(C_2-C_4)$alkoxy group then more preferably $R^3$ is a phenyl group substituted by a hydroxyethoxy group and wherein said phenyl group is optionally further substituted by one or more groups selected from methyl and Cl.

When $R^3$ is a phenyl group substituted by a hydroxy $(C_2-C_4)$alkoxy group then more preferably $R^3$ is a phenyl group substituted at the 2-position by a hydroxyethoxy group.

When $R^3$ is a phenyl group substituted by a hydroxy $(C_2-C_4)$alkoxy group then more preferably $R^3$ is a phenyl group substituted at the 2-position by a hydroxy$(C_2-C_3)$ alkoxy group and wherein said phenyl group is further substituted at the 4-position by one or more groups selected from OH, $(C_1-C_3)$alkoxy, $(C_1-C_3)$alkyl and halo.

When $R^3$ is a phenyl group substituted by a hydroxy $(C_2-C_4)$alkoxy group then more preferably $R^3$ is a phenyl group substituted at the 2-position by hydroxy$(C_2-C_3)$ alkoxy group and wherein said phenyl group is further substituted at the 5-position by one or more groups selected from OH, $(C_1-C_3)$alkoxy, $(C_1-C_3)$alkyl and halo.

When $R^3$ is a phenyl group substituted by a hydroxy $(C_1-C_4)$alkyl group the preferably $R^3$ is a phenyl group substituted by a hydroxy$(C_1-C_3)$alkyl group and wherein said phenyl group is optionally further substituted by one or more groups selected from OH, $(C_1-C_3)$alkoxy, $(C_1-C_3)$ alkyl and halo.

When $R^3$ is a phenyl group substituted by a hydroxy $(C_1-C_4)$alkyl group then more preferably $R^3$ is a phenyl group substituted by a hydroxy$(C_1-C_3)$alkyl group wherein said phenyl group is optionally further substituted by one or more groups selected from OH, methyl, ethyl, hydroxyethyl, hydroxymethyl, F and Cl.

When $R^3$ is a phenyl group substituted by a hydroxy $(C_1-C_4)$alkyl group then more preferably still $R^3$ is a phenyl group substituted by at the 3- or 4-positions by an hydroxy $(C_1-C_3)$alkyl group and wherein said phenyl group is optionally further substituted by one or more groups selected from OH, methyl, ethyl, F and Cl.

When $R^3$ is a phenyl group substituted by a hydroxy $(C_1-C_4)$alkyl group then more preferably still $R^3$ is a phenyl group substituted by at the 3- or 4-positions by a hydroxymethyl group and wherein said phenyl group is optionally further substituted at the 2-position by OH.

According to a further aspect the present invention provides compounds of formula (I) wherein $R^1$ is F, Cl or methyl; $R^2$ is H or F; and wherein $R^3$ is an optionally substituted C-linked pyrazole or imidazole group.

According to a further aspect the present invention provides compounds of formula (I) wherein $R^1$ is F, Cl or methyl; $R^2$ is H or F; and wherein $R^3$ is a phenyl group substituted by a hydroxy$(C_1-C_3)$alkyl group or a hydroxy $(C_2-C_3)$alkoxy group and wherein said phenyl group is optionally further substituted by one or more groups selected from OH, $(C_1-C_3)$alkoxy, $(C_1-C_3)$alkyl and halo.

Preferred compounds according to the present invention are selected from the group consisting of:

Syn-N-[4-(2-Hydroxy-5-hydroxymethyl-benzoylamino)-cyclohexyl]-5-methyl-2-(3-methylsulfanyl-phenoxy)-nicotinamide;

Syn-5-Fluoro-N-[4-(2-hydroxy-4-hydroxymethyl-benzoylamino)-cyclohexyl]-2-(3-methylsulfanyl-phenoxy)-nicotinamide;

Syn-5-Fluoro-N-(4-{[1-(2-hydroxy-ethyl)-1H-imidazole-4-carbonyl]-amino}-cyclohexyl)-2-(3-methylsulfanyl-phenoxy)-nicotinamide;

Syn-5-Fluoro-N-(4-{[3-(2-hydroxy-ethyl)-3H-imidazole-4-carbonyl]-amino}-cyclohexyl)-2-(3-methylsulfanyl-phenoxy)-nicotinamide;

Syn-5-Fluoro-N-(4-{[1-(2-hydroxy-ethyl)-1H-pyrazole-3-carbonyl]-amino}-cyclohexyl)-2-(3-methylsulfanyl-phenoxy)-nicotinamide;

Syn-5-Fluoro-N-(4-{[2-(2-hydroxy-ethyl)-2H-pyrazole-3-carbonyl]-amino}-cyclohexyl)-2-(3-methylsulfanyl-phenoxy)-nicotinamide;

Syn-5-Fluoro-N-(4-{[1-(2-hydroxy-ethyl)-1H-pyrazole-4-carbonyl]-amino}-cyclohexyl)-2-(3-methylsulfanyl-phenoxy)-nicotinamide;

Syn-5-Fluoro-N-(4-{[1-(2-hydroxy-ethyl)-5-methyl-1H-pyrazole-3-carbonyl]-amino}-cyclohexyl)-2-(3-methylsulfanyl-phenoxy)-nicotinamide;

Syn-5-Fluoro-2-(4-fluoro-3-methylsulfanyl-phenoxy)-N-{4-[2-(2-hydroxy-ethoxy)-benzoylamino]-cyclohexyl}-nicotinamide;

Syn-5-Fluoro-N-(4-{[1-(2-hydroxy-ethyl)-5-isopropyl-1H-pyrazole-3-carbonyl]-amino}-cyclohexyl)-2-(3-methylsulfanyl-phenoxy)-nicotinamide;

Syn-5-Fluoro-N-{4-[2-(2-hydroxy-ethoxy)-5-methyl-benzoylamino]-cyclohexyl}-2-(3-methylsulfanyl-phenoxy)-nicotinamide;

Syn-5-Fluoro-N-{4-[2-(2-hydroxy-ethoxy)-4-methyl-benzoylamino]-cyclohexyl}-2-(3-methylsulfanyl-phenoxy)-nicotinamide;

Syn-5-Fluoro-N-{4-[2-(2-hydroxy-ethoxy)-3-methyl-benzoylamino]-cyclohexyl}-2-(3-methylsulfanyl-phenoxy)-nicotinamide;

Syn-N-{4-[5-Chloro-2-(2-hydroxy-ethoxy)-benzoylamino]-cyclohexyl}-5-fluoro-2-(3-methylsulfanyl-phenoxy)-nicotinamide;

Syn-N-{4-[4-Chloro-2-(2-hydroxy-ethoxy)-benzoylamino]-cyclohexyl}-5-fluoro-2-(3-methylsulfanyl-phenoxy)-nicotinamide;

Syn-N-{4-[3-Chloro-2-(2-hydroxy-ethoxy)-benzoylamino]-cyclohexyl}-5-fluoro-2-(3-methylsulfanyl-phenoxy)-nicotinamide;

Syn-N-(4-{[5-Ethyl-1-(2-hydroxy-ethyl)-1H-pyrazole-3-carbonyl]-amino}-cyclohexyl)-5-fluoro-2-(3-methylsulfanyl-phenoxy)-nicotinamide; or Syn-5-Chloro-N-{4-[2-(2-hydroxy-ethoxy)-benzoylamino]-cyclohexyl}-2-(3-methylsulfanyl-phenoxy)-nicotinamide and pharmaceutically acceptable salts, solvates, polymorphs and pro-drugs thereof.

Finally, more preferred compounds herein are selected from the group consisting of:

Syn-5-Fluoro-N-(4-{[1-(2-hydroxy-ethyl)-1H-pyrazole-3-carbonyl]-amino}-cyclohexyl)-2-(3-methylsulfanyl-phenoxy)-nicotinamide;

Syn-5-Fluoro-N-(4-{[1-(2-hydroxy-ethyl)-5-methyl-1H-pyrazole-3-carbonyl]-amino}-cyclohexyl)-2-(3-methylsulfanyl-phenoxy)-nicotinamide;

Syn-5-Fluoro-2-(4-fluoro-3-methylsulfanyl-phenoxy)-N-{4-[2-(2-hydroxy-ethoxy)-benzoylamino]-cyclohexyl}-nicotinamide;

Syn-5-Fluoro-N-{4-[2-(2-hydroxy-ethoxy)-5-methyl-benzoylamino]-cyclohexyl}-2-(3-methylsulfanyl-phenoxy)-nicotinamide;

Syn-5-Fluoro-N-{4-[2-(2-hydroxy-ethoxy)-4-methyl-benzoylamino]-cyclohexyl}-2-(3-methylsulfanyl-phenoxy)-nicotinamide;

Syn-N-(4-{[5-Ethyl-1-(2-hydroxy-ethyl)-1H-pyrazole-3-carbonyl]-amino}-cyclohexyl)-5-fluoro-2-(3-methylsulfanyl-phenoxy)-nicotinamide; or Syn-5-Chloro-N-{4-[2-(2-hydroxy-ethoxy)-benzoylamino]-cyclohexyl}-2-(3-methylsulfanyl-phenoxy)-nicotinamide and pharmaceutically acceptable salts, solvates, polymorphs and pro-drugs thereof.

The present invention additionally provides compounds of formula (I) wherein $R^1$, $R^2$, and $R^3$ are as previously defined and wherein the optional substituent groups of $R^3$ additionally comprise hydroxymethoxy.

It has been found that these nicotinamide derivatives are inhibitors of PDE4 isoenzymes, particularly useful for the treatment of inflammatory, respiratory and allergic diseases and conditions or for wounds.

In the here above general formula (I), halo denotes a halogen atom selected from the group consisting of fluoro (F), chloro (Cl), bromo (Br) and iodo (I) in particular fluoro or chloro.

$(C_1-C_3)$alkyl or $(C_1-C_4)$alkyl or $(C_2-C_4)$alkyl radicals denote a straight-chain or branched group containing respectively 1 to 3 or 1 to 4 or 2 to 4 carbon atoms. This also applies if they carry substituents or occur as substituents of other radicals, for example in $(C_1-C_4)$alkoxy radicals, hydroxy$(C_1-C_4)$alkyl and hydroxy$(C_2-C_4)$alkoxy radicals. Examples of suitable $(C_1-C_3)$alkyl and $(C_1-C_4)$alkyl radicals are methyl, ethyl, n-propyl, iso-propyl, n-butyl, iso-butyl, sec-butyl and tert-butyl. Examples of suitable $(C_1-C_4)$alkoxy and $(C_2-C_4)$alkoxy radicals are methoxy, ethoxy, n-propyloxy, iso-propyloxy, n-butyloxy, iso-butyloxy, sec-butyloxy and tert-butyloxy. Hydroxy$(C_1-C_4)$alkyl and hydroxy$(C_2-C_4)$alkoxy radicals may contain more than one hydroxy group (—OH). According to a preferred embodiment of, said invention, such radicals contain one hydroxy substituent. Examples of suitable hydroxy$(C_1-C_4)$alkyl radicals are hydroxymethyl, 1-hydroxyethyl or 2-hydroxyethyl.

In the hereabove general formula (I), a "C-linked 5- or 6-membered heteroaryl containing 1, 2 or 3 nitrogen atoms" means a monocyclic aromatic ring having 5 or 6 ring members, which contains 1, 2 or 3 nitrogen (N) atom(s) depending in number and quality of the total number of ring members. Said heteroaryl radicals can also be unsubstituted, monosubstituted or polysubstituted, as indicated in the definition of $R^3$ hereabove for general formula (I) according to the present invention. Any suitable 5- or 6-membered heteroaryl containing from 1 to 3 nitrogen (N) atoms may be used. Examples of suitable heteroaryls are pyrrole, pyridine, pyrazine, pyridazine, pyrazole and imidazole. According to a preferred aspect, said heteroaryl is selected from pyrazole and imidazole.

Nitrogen heterocyclic radicals can also be present as N-oxides or as quaternary salts.

In the general formula (I) according to the present invention, when a radical is mono- or poly-substituted, said substituent(s) can be located at any desired position(s). Also, when a radical is polysubstituted, said substituents can be identical or different, unless otherwise stated.

The nicotinamide derivatives of the formula (I) can be prepared using conventional procedures such as by the following illustrative methods in which $R^1$, $R^2$ and $R^3$ are as previously defined for the nicotinamide derivatives of the formula (I) unless otherwise stated.

The compounds of formula (I) may be prepared by the methods disclosed hereunder, and exemplified in the Examples and Preparations. Other methods may be used in accordance with the skilled person's knowledge.

Unless otherwise provided herein:

PyBOP® means Benzotriazol-1-yloxytris(pyrrolidino) phosphonium hexafluorophosphate;

PyBrOP® means bromo-tris-pyrrolidino-phosphonium hexafluoro-phosphate;

CDI means N,N'-carbonyldiimidazole;

WSCDI means 1-(3-dimethylaminopropyl)-3-ethylcarbodiimide hydrochloride;

Mukaiyama's reagent means 2-chloro-1-methylpyridinium iodide;

HATU means O-(7-Azabenzotriazol-1-yl)-N,N,N'N'-tetramethyluronium hexafluorophosphate;

HBTU means O-Benzotriazol-1-yl-N,N,N'N'-tetramethyluronium hexafluorophosphate;

DCC means N,N'-dicyclohexylcarbodiimide;

CDI means N,N'-carbonyidiimidazole;

HOAT means 1-hydroxy-7-azabenzotriazole;

HOBT means 1-hydroxybenzotriazole hydrate;

Hünig's base means N-ethyldiisopropylamine;

$Et_3N$ means triethylamine;

NMM means N-methylmorpholine;

NMP means 1-methyl-2-pyrrolidinone;

DMAP means 4-dimethylaminopyridine;
NMO means 4-methylmorpholine N-oxide;
KHMDS means potassium bis(trimethylsilyl)amide;
NaHMDS means sodium bis(trimethylsilyl)amide;
DIAD means diisopropyl azodicarboxylate;
DEAD means diethyl azodicarboxylate;
DIBAL means diisobutylammonium hydride;
Dess-Martin periodinane means 1,1,1-triacetoxy-1,1-dihydro-1,2-benziodoxol-3(1H)-one;
TBDMS-Cl means tert-butyldimethylchlorosilane;
TMS-Cl means chlorotrimethylsilane;
Boc means tert-butoxycarbonyl;
CBz means benzyloxycarbonyl;
MeOH means methanol, EtOH means ethanol, and EtOAc means ethyl acetate;
THF means tetrahydrofuran; DMSO means dimethyl sulphoxide; DCM means dichloromethane; DMF means N,N-dimethylformamide; AcOH means acetic acid; TFA means trifluoroacetic acid; RT means room temperature; 3° means tertiary; eq means equivalents; Me means methyl; Et means ethyl; Bn means benzyl; other abbreviations are used in accordance with standard synthetic chemistry practice.

Route A

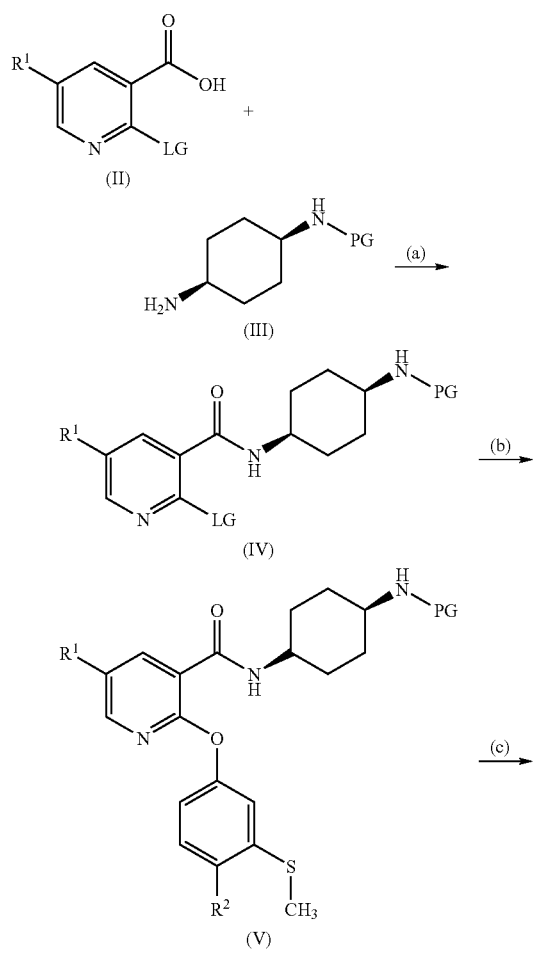

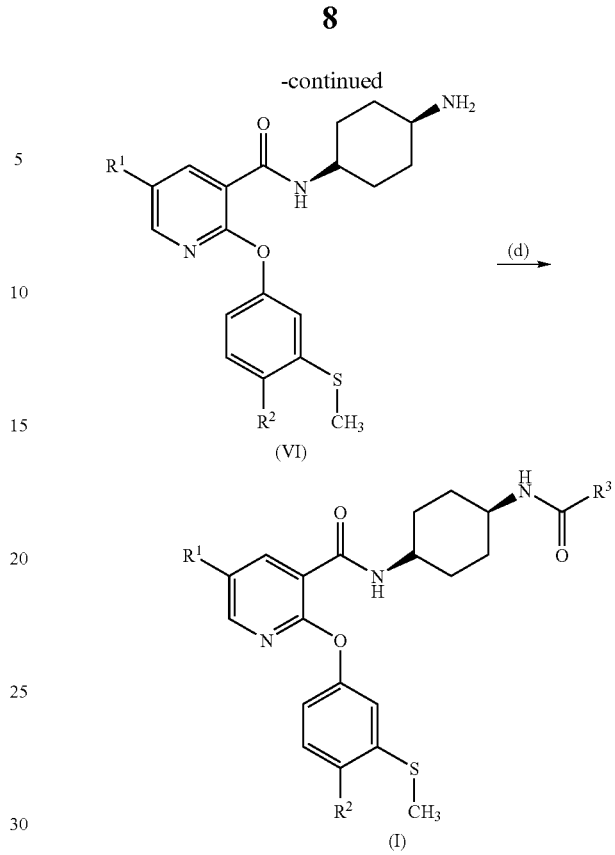

Nicotinic acids or acid derivatives of formula (II) are either available commercially or may be obtained by analogy with the methods of Haylor et. al. (EP 0634413, examples 9 and 10, pages 12–13), or Marzi et. al. (European Journal of Org. Chem. 2001 (7), 1371–1376). The protected syn-cyclohexane-1,4 diamnes of formula (III) are either available commercially or may be prepared by analogy with the method of Oku et al (WO 99/54284, for example, at page 80, preparation 77(1)).

In the scheme above, $R^1$, $R^2$ and $R^3$ are as previously defined, PG is a suitable amine protecting group, typically Boc, TFA, CBz and preferably Boc, and LG is a suitable leaving group, typically halo, and preferably Cl.

Step (a)—Acid-amine Coupling.

This acid/amine coupling may be undertaken by using either:
(i) an acyl chloride derivative of acid (II)+amine (III), with an excess of acid acceptor in a suitable solvent; or
(ii) the acid or acid derivative (II) with a conventional coupling agent+amine (III), optionally in the presence of a catalyst, with an excess of acid acceptor in a suitable solvent.

Typically the conditions are as follows:
(i) acid chloride of acid (II) (generated in-situ), an excess of amine (III), optionally with an excess of 3° amine such as $Et_3N$, Hünig's base or NMM, in DCM or THF, without heating for 1 to 24 hrs;
(ii) acid (II), WSCDI/DCC/CDI optionally in the presences of HOBT/HOAT, an excess of amine (III), with an excess of NMM, $Et_3N$, Hünig's base in THF, DCM or EtOAc, at RT for 4 to 48 hrs; or, acid (II), PYBOP®/PyBrOP®/Mukaiyama's reagent, an excess of amine (III), with an excess of NMM, $Et_3N$, Hünig's base in THF, DCM or EtOAc, at RT for 4 to 24 hrs; or (iii) acid (II), CDI and amine in DMF at RT for 72 hours.

The preferred conditions are: either treatment of (II) with oxalyl chloride and catalytic DMF in DCM at RT for 3 hours followed by the addition of Hünig's base or Et₃N and the amine and stirring at RT for 18 hours; or treatment of (II) with CDI in DMF at RT for 1 hour followed by the addition of the amine and stirring at RT for 72 hours.

Step (b)—Ether Formation

Substitution of the leaving group, LG, wherein said leaving group is for example a halogen and is preferably chlorine, of the compound (IV) with an excess of a substituted phenol to give compounds of formula (V).

Compounds of general formula (V) can be prepared from compounds of general formula (IV) via treatment with a suitable base, in a suitable solvent, in the presence of optionally substituted, 3-methylsulphanyl-phenol. Alkali metal salts are used as the base (e.g. $Cs_2CO_3$, $K_2CO_3$, NaOH) and MeCN, or dioxan are suitable solvents for use. The reaction is carried out at elevated temperature.

Preferred conditions are: reaction of compound (IV), wherein the LG is chlorine, with an excess of optionally substituted, 3-methylsulphanyl-phenol in the presence of caesium carbonate in dioxan or MeCN at about 100° C., optionally at reflux temperatures, for from about 24 to about 72 hours. Exemplified herein by preparation 43.

Step (c)—Removal of Protecting Group

Deprotection of the N protecting group (PG), from compounds of general formula (V) to provide compounds of general formula (VI) is undertaken using standard methodology, as described in "Protective Groups in Organic Synthesis" by T. W. Greene and P. Wutz.

For example when PG is Boc, the preferred conditions are: treatment of compound (V) with a strong acid (e.g. TFA, HCl), in a suitable solvent such as for example dioxan or DCM at room temperature. Preferred conditions herein for removal of a Boc group are: either treatment with hydrochloric acid (preferably 4M HCl) in dioxan at RT for about 5 hrs; or bubbling HCl gas through a solution of (V) in DCM for about 2 hours followed by stirring at RT for about 48 hours. Exemplified herein as preparation 44.

Step (d)—Reaction of De-protected Amino Group with $R^3COOH$

Compounds of the general formula (I) may be prepared by reaction of amines of is general formula (VI) via treatment with a suitable acid of formula $R^3COOH$ according to the general methods described previously for Route A, step (a).

Preferred conditions for this conversion are treatment of a solution of amine (VI) in NMP or DCM, and optionally with DMF for solubility, with the appropriate acid, $R^3COOH$ in the presence of WSCDI, HOBT and NMM or Hünig's base, at RT for from about 18 to about 40 hours.

The transformation of (VI) to (I) is exemplified by Examples 1 and 2.

Route B

Alternatively, compounds of formula (I) may be prepared by Route B:

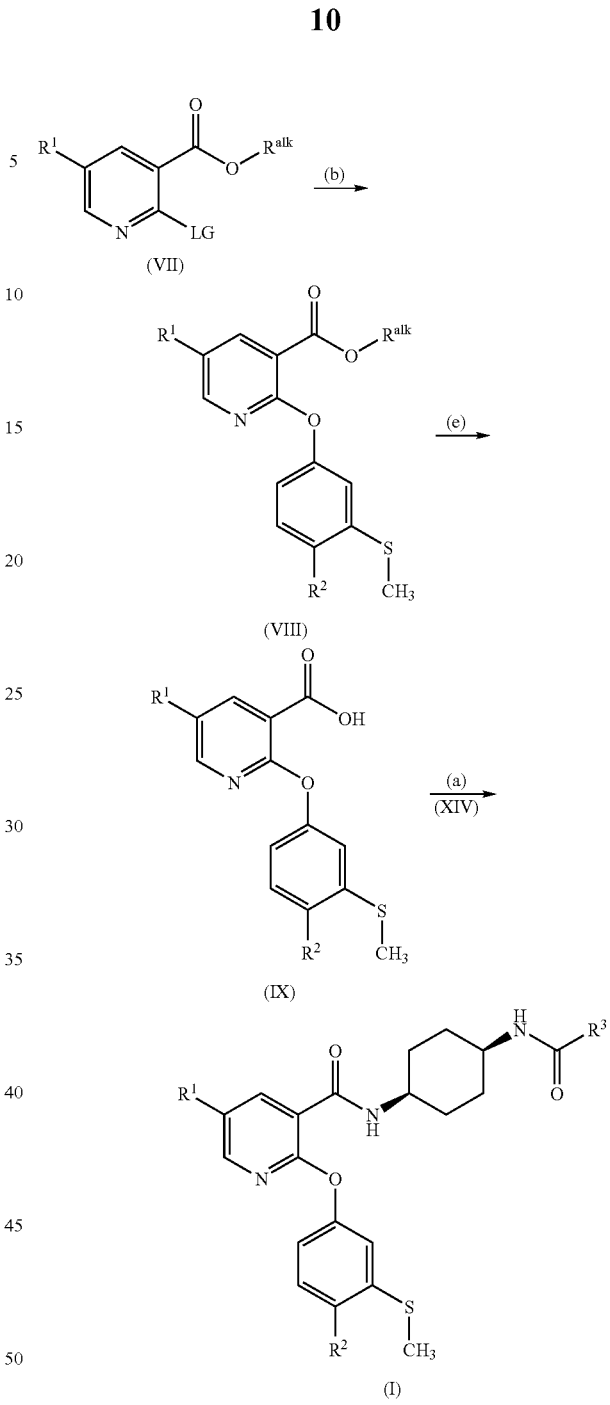

$R^{alk}$ represents a $C_1$–$C_4$ alkyl group or Bn, preferably a $C_1$–$C_3$ alkyl group and more preferably Et.

Compounds of formula (VII) are either available commercially or may be obtained from the compounds of formula (II), using standard esterification conditions. The protected amines of formula (III) are either available commercially or may be prepared by analogy with the method of Oku et. al. (WO 99/54284) as described hereinbefore.

Compounds of formula (VIII) may be prepared by reaction of the ester (VII) with optionally substituted, 3-methylsulphanyl-phenol, as descibed previously in step (b), Route A. Suitable optional catalysts for use in this reaction include CuI. Preferred herein are compounds of formula (III) wherein LG is halo and is preferably chlorine. Preferred conditions for use herein are treatment with caesium carbonate in dioxan at about 100° C. for about 48 hours. Exemplified herein by preparation 38.

Step (e)—Ester Hydrolysis

Hydrolysis of the ester (VIII) may be achieved in the presence of acid or base, in a suitable solvent, optionally at elevated temperature to afford the acid (IX). Typically, the ester (VIII) is treated with a solution of a suitable base such as an alkali metal hydroxide (eg LiOH, NaOH, CsOH) in aqueous solvent (MeOH, EtOH, THF) at RT, to give the acid (IX). Preferred conditions herein provide for treatment of ester (VIII) in THF with a 1M aqueous solution of LiOH at RT for about 24 hours. Exemplified herein by preparation 39.

Alternatively compounds of formula (IX) may be prepared from compounds of formula (II) by reaction with optionally substituted 3-methylsulphanyl-phenol, as described previously in step (b), Route A.

Reaction of the acid of formula (IX) with the amine of formula (XIII) as described hereinafter in Route C, step (d) provides the compounds of formula (I). Reaction of the acid of formula (IX) with the amine of formula (III) as described previously in Route A, step (a) provides the compounds of formula (V) which can be converted to provide compounds of formula (I) as detailed in Route A, steps (c) and (d). Preferred conditions herein for formation of compounds of formula (I) from the corresponding acid of formula (IX) are either: treatment of acid (IX) in catalytic DMF in DCM with oxalyl chloride for about 3 hours at RT (to form the acid chloride), followed by the addition of Hünig's base or Et$_3$N and the amine (XII) and stirring at RT for about 18 hours; or treatment of acid (IX) with CDI in DMF at RT for about 1Hour followed by addition of the amine (XII) and stirring for up to about 72 hours.

Compounds of formula (V) as described in Route A, may alternatively be prepared by reaction of acid (IX) with the protected amine (III), according to the methods described for step (a), of Route A.

Such amine compounds of formula (V) can be de-protected by the methods described in Route A, step,(c) and subsequently reacted with a suitable acid of formula R$^3$OOH as described in Route A, step (d) to provide compounds of formula (I).

Route C illustrates the preparation of carboxylic acids of the formula QR$^3$COOH, where Q=THP:

Route C

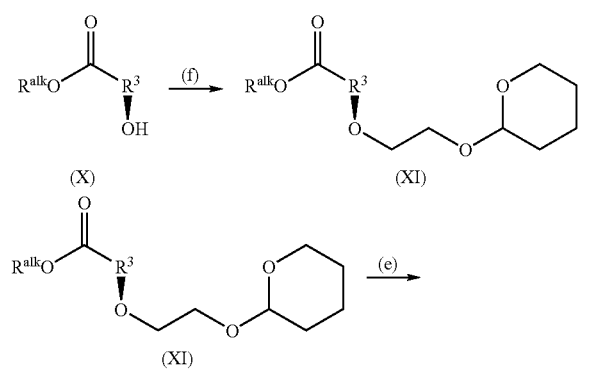

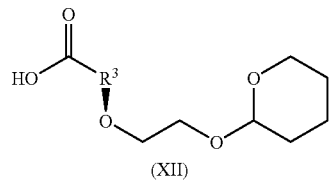

$R^3$ and $R^{alk}$ are as previously defined herein.

(f)—Introduction of Hydroxyl Protecting Group

Protection of the hydroxyl function of compound (X) can be achieved by any standard methodology. Preferred herein is protection via introduction of a THP protecting group. Preferred conditions for such transformation are: Treatment of (X) with K$_2$CO$_3$ and catalytic KI and 2(2-bromoethoxy) tetrahydro-2H-pyran in is MeCN at about 90° C. for about 72 hours.

(e)—Hydrolysis

Removal of acid protecting group, R (e.g. lower alkyl, Bz, typically lower alkyl, preferably methyl or ethyl), from ester (XI) to give carboxylic acid (XII) can be achieved as described for Step (e), Route B. Preferred conditions for such transformation wherein R$^{alk}$ is C$_1$–C$_4$ are: treatment of (XI) with either an aqueous solution of LiOH in THF or an aqueous solution of NaOH in EtOH at RT for about 72 hours.

Route D

Compounds of general formula (I) may alternatively be prepared by the following route.

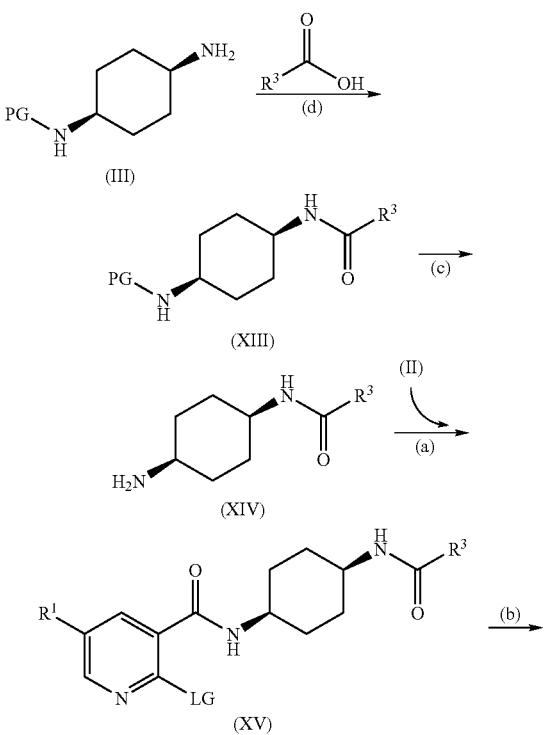

-continued

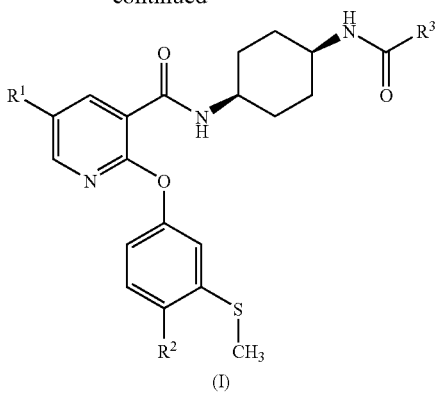

(I)

The compound of formula (XIII) may be prepared from the amine (III) by reaction with $R^3COOH$ according to the methods described previously in step (d), Route A.

The de-protected amine compound of general formula (XIV) may be prepared from the protected amine compound of general formula (XII) via removal of the protecting group PG, preferably a Boc group, by analogy to the methods described previously in step (c), Route A.

The amide compounds of general formula (XV) may be prepared by reaction of the amine of general formula (XIV) with the acid or acid derivative (II) according to the methods described previously in steps (a) and (d), Route A.

Compounds of formula (I) may be prepared by substitution of the leaving group, LG, of the compounds of formula (XV) by an optionally substituted, 3-methylsulphanyl-phenol group as described previously in step (b), Route A.

Further Routes

Certain $R^3$ groups may undergo further functional group interconversions (FGIs) and transformations, such as alkylation of a hydroxy substituent group, using a suitable alkylbromide, in the presence of a suitable alkali metal base (such as $K_2CO_3$), optionally in the presence of a catalyst (eg KI) in a suitable solvent such as acetonitrile and/or N,N-dimethylformamide at elevated temperature, or demethylation of a methoxy group by treatment with lithium iodide in pyridine or collidine, or by treatment with $BBr_3$ in dichloromethane.

As detailed hereinbefore for certain compounds of the description, a suitable protecting group strategy may be employed. For example, a hydroxyl group may be protected using a tetrahydropyran group, and deprotection may be achieved by treatment with a solution of acetic acid:water:tetrahydrofuran (4:1:2 by volume) at RT for up to 18 hrs. Further, a benzyloxy group may be used and deprotected to give the corresponding hydroxyl compound, for example by using a reduction (e.g. with palladium black in acid).

For example, reaction of amine (VI) with a carboxylic acid of the formula, $QR^3COOH$, wherein Q is an alcohol protecting group (eg THP or phenyl, preferably THP), to provide a protected amide can be carried out as described in step (c) of Scheme A. Preferred conditions for such reaction are: treatment of a solution of amine (VI) in DCM, and optionally DMF for solubility, with acid $QR^3COOH$ in the presence of HOBT, WSCDI and NMM or Hünig's base, optionally with catalytic DMF, at RT for from about 18 to about 40 hours.

Removal of protecting group, Q, from the protected amide can be achieved by a standard method specific for that protecting group, as described in "Protective Groups in Organic Synthesis" by T. W. Greene and P. Wutz. Preferred conditions for use herein when Q=THP are: treatment of (XIII) with a AcOH:THF:water (4:2:1 by volume) mixture at about 60° C. for about 24 hours. Protection/deprotection strategies are exemplified by Preparation 19 and in Examples 3 to 9 herein.

Optionally, where appropriate, steps both the coupling step and the de-protection step may be combined in a "one pot" reaction to synthesise compounds of formula (I) from either compounds of formula (VI) or (IX) directly.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the examples and preparations hereto.

For some of the steps of the here above described process of preparation of the nicotinamide derivatives of formula (I), it can be necessary to protect the potential reactive functions that are not wished to react. In such a case, any compatible protecting radical can be used. In particular methods such as those described by T. W. GREENE (*Protective Groups in Organic Synthesis*, A. Wiley-Interscience Publication, 1981) or by McOMIE (*Protective Groups in Organic Chemistry*, Plenum Press, 1973), can be used.

Also, the nicotinamide derivatives of formula (I) as well as intermediate for the preparation thereof can be purified according to various well-known methods, such as for example crystallization or chromatography.

Thus according to a further embodiment the present invention provides a process for the preparation of a nicotinamide derivative of the formula (I) as described in claim 1 comprising:

(i) reaction of amines of general formula (VI) via treatment with a suitable acid of formula $R^3COOH$; or (ii) substitution of the leaving group, LG, of the compounds of formula (XV) by an optionally substituted, 3-methylsulphanyl-phenol group; or (iii) reaction of the acid of formula (IX) with the amine of formula (III) to provide compound of formula (V) and subsequent deptotection; or (iv) reaction of the acid of formula (IX) with the amine of formula (XIV)

wherein formulae (VI), (IX), (III), (V), (XV) and (XIV) are as defined hereinbefore.

The present invention additionally provides compounds of the general formulae (V), (VI), (IX), (XV) and (XIV) as defined hereinbefore.

According to a yet further embodiment the present invention provides processes for the preparation of compounds of general formulae (VI), (IX) and (XII) wherein said processes are as illustrated by steps (a), (b) and (c) Route A, steps (c) and (a) Route B and steps (b) and (e) Route C herein.

The nicotinamide derivatives of formula (I) may also be optionally transformed in pharmaceutically acceptable salts. In particular, these pharmaceutically acceptable salts of the nicotinamide derivatives of the formula (I) include the acid addition and the base salts (including disalts) thereof.

Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodie, hydrogen phosphate, isethionate, D- and L-lactate, malate, maleate, malonate, mesylate, methylsulphate, 2-napsylate, nicotinate, nitrate, orotate, palmoate, phosphate, saccharate, stearate, succinate sulphate, D- and L-tartrate, 1-hydroxy-2-naphtoate, 3-hydroxy-2-naphthoate and tosylate saltes.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection and Use, Wiley-VCH, Weinheim, Germany (2002).

A pharmaceutically acceptable salt of a nicotinamide derivative of the formula (I) may be readily prepared by mixing together solutions of the nicotinamide derivative of formula (I) and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Also within the scope of the invention are clathrates, drug-host inclusion complexes wherein, in contrast to the aforementioned solvates, the drug and host are are present in non-stoichiometric amounts. For a review of such complexes, see J Pharm Sci, 64 (8), 1269–1288 by Haleblian (August 1975).

Hereinafter all references to nicotinamide derivatives of formula (I) include references to salts thereof and to solvates and clathrates of compounds of formula (I) and salts thereof.

The invention includes all polymorphs of the nicotinamide derivatives of formula (I).

Also within the scope of the invention are so-called "prodrugs" of the nicotinamide derivatives of formula (I). Thus certain derivatives of nicotinamide derivatives of formula (I) which have little or no pharmacological activity themselves can, when metabolised upon administration into or onto the body, give rise to nicotinamide derivatives of formula (I) having the desired activity. Such derivatives are referred to as "prodrugs".

Prodrugs in accordance with the invention can, for example, be produced by replacing appropriate functionalities present in the nicotinamide derivatives of formula (I) with certain moieties known to those skilled in the art as "pro-moieties" as described, for example, in "Design of Prodrugs" by H Bundgaard (Elsevier, 1985).

Finally, certain nicotinamide derivatives of formula (I) may themselves act as prodrugs of other nicotinamide derivatives of formula (I).

Nicotinamide derivatives of formula (I) containing one or more asymmetric carbon atoms can exist as two or more optical isomers. Where a nicotinamide derivative of formula (I) contains an alkenyl or alkenylene group, geometric cis/trans (or Z/E) isomers are possible, and where the nicotinamide derivative contains, for example, a keto or oxime group, tautomeric isomerism ('tautomerism') may occur. It follows that a single nicotinamide derivative may exhibit more than one type of isomerism.

Included within the scope of the present invention are all optical isomers, geometric isomers and tautomeric forms of the nicotinamide derivatives of formula (I), including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of a nicotinamide derivative of formula (I). An isotopic variation is defined as one in which at least one atom is replaced by an atom having the same atomic number, but an atomic mass different from the atomic mass usually found in nature.

Examples of isotopes suitable for inclusion in the nicotinamide derivatives of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulphur, such as $^{35}S$, fluorine, such as $^{18}F$, and chlorine, such as $^{36}Cl$.

Substitution of the nicotinamide derivative of formula (I) isotopes such as deuterium, i.e. $^2H$, may afford certain therapeutic advantages resulting from greater metabolic stability, for example, increased in vivo half-life or reduced dosage requirements, and hence may be preferred in some circumstances.

Certain isotopic variations of the nicotinamide derivatives of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Isotopic variations of the nicotinamide derivatives of formula (I) can generally be prepared by conventional techniques known to those skilled in the art or by processes analogous to those described in the accompanying Examples and Preparations using appropriate isotopic variations of suitable reagents.

According to a further aspect, the present invention concerns mixtures of nicotinamide derivatives of the formula (I), as well as mixtures with or of their pharmaceutically acceptable salts, solvates, polymorphs, isomeric forms and/or isotope forms.

According to the present invention, all the here above mentioned forms of the nicotinamide derivatives of formula (I) except the pharmaceutically acceptable salts (i.e. said solvates, polymorphs, isomeric forms and isotope forms), are defined as "derived forms" of the nicotinamide derivatives of formula (I) in what follows.

The nicotinamide derivatives of formula (I), their pharmaceutically acceptable salts and/or derived forms, are valuable pharmaceutical active compounds, which are suitable for the therapy and prophylaxis of numerous disorders in which the PDE4 enzymes are involved, in particular the inflammatory disorders, allergic disorders, respiratory diseases and wounds.

The nicotinamide derivatives of formula (I) and their pharmaceutically acceptable salts and derived forms as mentioned above can be administered according to the invention to animals, preferably to mammals, and in particular to humans, as pharmaceuticals for therapy or prophylaxis. They can be administered per se, in mixtures with one another or in combination with other drugs, or in the form of pharmaceutical preparations which permit enteral (gastric) or parenteral (non-gastric) administration and which as active constituent contain an efficacious dose of at least one nicotinamide derivative of the formula (I), its pharmaceutically acceptable salts and/or derived forms, in addition to customary pharmaceutically innocuous excipients and/or additives. The term "excipient" is used herein to describe any ingredient other than the compound of the invention. The choice of excipient will to a large extent depend on the particular mode of administration.

The nicotinamide derivatives of formula (I), their pharmaceutically acceptable salts and/or derived forms may be freeze-dried, spray-dried, or evaporatively dried to provide a solid plug, powder, or film of crystalline or amorphous material. Microwave or radio frequency drying may be used for this purpose.

Oral Administration

The nicotinamide derivatives of formula (I) their pharmaceutically acceptable salts and/or derived forms of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The nicotinamide derivatives of formula (I), their pharmaceutically acceptable salts and/or derived forms of the invention may also be used in fast-dissolving, fast-disintegrating dosage forms such as those described in Expert Opinion in Therapeutic Patents, 11 (6), 981–986 by Liang and Chen (2001).

The composition of a typical tablet in accordance with the invention may comprise:

| Ingredient | % w/w |
| --- | --- |
| Nicotinamide derivative of formula (1) | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1–14 (2001). Other modified release formulations are described in U.S. Pat. No. 6,106,864.

Parenteral Administration

The nicotinamide derivatives of formula (I), their pharmaceutically acceptable salts and/or derived forms of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of nicotinamide derivatives of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Topical Administration

The nicotinamide derivatives of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, J Pharm Sci, 88 (10), 955–958 by Finnin and Morgan (October 1999).

Other means of topical administration include delivery by iontophoresis, electroporation, phonophoresis, sonophoresis and needle-free or microneedle injection.

Formulations for topical administration may be formulated to be immediate and/or modified release. Modified release formulations include delayed-, sustained-, pulsed-, controlled dual-, targeted and programmed release. Thus nicotinamide derivatives of formula (I) may be formulated in a more solid form for administration as an implanted depot providing long-term release of the active compound.

Inhaled/Intranasal Administration

The nicotinamide derivatives of formula (I) can also be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 µg to 20 mg of the nicotinamide derivative of formula (I) per actuation and the actuation volume may vary from 1 µl to 100 µl. A typical formulation may comprise a nicotinamide derivative of formula (I), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as I-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff" containing from 1 µg to 4000 µg of the nicotinamide derivative of formula (I). The overall daily dose will typically be in the range 1 µg to 20 mg which may be administered in a single dose or, more usually, as divided doses throughout the day.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

Flavouring agents, such as methol and levomethol and/or sweeteners such as saccharing or saccharin sodium can be added to the formulation.

Rectal/Intravaginal Administration

The nicotinamide derivatives of formula (I) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

Ocular/Andial Administration

The nicotinamide derivatives of formula (I) may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes., A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/andial administration may be formulated to be immediate and/or modified release. Modified release formulations include delayed-, sustained-, pulsed-, controlled dual-, targeted, or programmed release.

Enabling Technologies

The nicotinamide derivatives of formula (I) may be combined with soluble macromolecular entities such as cyclodextrin or polyethylene glycol-containing polymers to improve their solubility, dissolution rate, taste-masking, bioavailability and/or stability.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the nicotinamide derivatives of formula (I) is typically in the range 0.001 mg/kg to 100 mg/kg depending, of course, on the mode of administration. The total daily dose may be administered in single or divided doses. The physician will readily be able to determine doses for subjects depending on age, weight, health state and sex or the patient as well as the severity of the disease.

According to another embodiment of the present invention, the nicotinamide derivatives of the formula (I), their pharmaceutically acceptable salts and/or their derived forms, can also be used as a combination with one or more additional therapeutic agents to be co-administered to a patient to obtain some particularly desired therapeutic end result. The second and more additional therapeutic agents may also be a nicotinamide derivatives of the formula (I), their pharmaceutically acceptable salts and/or their derived forms, or one or more PDE4 inhibitors known in the art. More typically, the second and more therapeutic agents will be selected from a different class of therapeutic agents.

As used herein, the terms "co-administration", "co-administered" and "in combination with", referring to the nicotinamide derivatives of formula (I) and one or more other therapeutic agents, is intended to mean, and does refer to and include the following:

simultaneous administration of such combination of nicotinamide derivative(s) and therapeutic agent(s) to a patient in need of treatment, when such components are formulated together into a single dosage form which releases said components at substantially the same time to said patient, substantially simultaneous administration of such combination of nicotinamide derivative(s) and therapeutic agent(s) to a patient in need of treatment, when such components are formulated apart from each other into separate dosage forms which are taken at substantially the same time by said patient, whereupon said components are released at substantially the same time to said patient, sequential administration of such combination of nicotinamide derivative(s) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of nicotinamide derivative(s) and therapeutic agent(s) to a patient in need of treatment, when such components are formulated together into a single dosage form which releases said components in a controlled manner whereupon they are concurrently, consecutively, and/or overlappingly administered at the same and/or different times by said patient.

Suitable examples of other therapeutic agents which may be used in combination with the nicotinamide derivatives of the formula (I), their pharmaceutically acceptable salts and/or their derived forms include, but are by no mean limited to:

(a) 5-Lipoxygenase (5-LO) inhibitors or 5-lipoxygenase activating protein (FLAP) antagonists,
(b) Leukotriene antagonists (LTRAs) including antagonists of LTB4, LTC4, LTD4, and LTE4,
(c) Histaminic receptor antagonists including H1, H3 and H4 antagonists,
(d) α1- and α2-adrenoceptor agonist vasoconstrictor sympathomimetic agents for decongestant use,
(e) Muscarinic M3 receptor antagonists or anticholinergic agents,
(f) β2-adrenoceptor agonists,
(g) Theophylline,
(h) Sodium cromoglycate,
(i) COX-1 inhibitors (NSAIDs) and COX-2 selective inhibitors,
(j) Oral or inhaled Glucocorticosteroids,
(k) Monoclonal antibodies active against endogenous inflammatory entities,
(l) Anti-tumor necrosis factor (anti-TNF-a) agents,
(m) Adhesion molecule inhibitors including VLA-4 antagonists,
(n) Kinin-B1- and B2-receptor antagonists,
(o) Immunosuppressive agents,
(p) Inhibitors of matrix metalloproteases (MMPs),
(q) Tachykinin NK1, NK2 and NK3 receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFkb pathway, e.g. IKK inhibitors,
(w) Agents that can be classed as mucolytics or anti-tussive,
(x) antibiotics, and
(y) p38 MAP kinase inhibitors According to the present invention, combination of the nicotinamide derivatives of formula (I) with:

muscarinic M3 receptor agonists or anticholinergic agents including in particular ipratropium salts, namely bromide, tiotropium salts, namely bromide, oxitropium salts, namely bromide, perenzepine, and telenzepine, H3 antagonists, β2-adrenoceptor agonists including albutarol, salbutamol, formoterol and salmeterol, glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, and mometasone furoate, p38 MAP kinase inhibitors, or adenosine A2a receptor agonists, are preferred.

It is to be appreciated that all references herein to treatment include curative, palliative and prophylactic treatment. The description which follows concerns the therapeutic applications to which the nicotinamide derivatives of formula (I) may be put.

The nicotinamide derivatives of formula (I) inhibit the PDE4 isozyme and thereby have a wide range of therapeutic applications, as described further below, because of the essential role, which the PDE4 family of isozymes plays in the physiology of all mammals. The enzymatic role performed by the PDE4 isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE4 inhibition plays a significant role in a variety of physiological processes. There is extensive literature in the art describing the effects of PDE inhibitors on various inflammatory cell responses, which in addition to cAMP increase, include inhibition of superoxide production, degranulation, chemotaxis and tumor necrosis factor (TNF) release in eosinophils, neutrophils and monocytes.

Therefore, a further aspect of the present invention relates to the use of the nicotinamide derivatives of formula (I), their pharmaceutically acceptable salts and/or derived forms, in the treatment of diseases, disorders, and conditions in which the PDE4 isozymes are involved. More specifically, the present invention also concerns the use of the nicotinamide derivatives of formula (I), their pharmaceutically acceptable salts and/or derived forms, in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma and wheezy infant syndrome, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated therewith, COPD that is characterized by irreversible, progressive airways obstruction, adult respiratory distress syndrome (ARDS) and exacerbation of airways hyperreactivity consequent to other drug therapy pneumoconiosis of whatever type, etiology, or pathogenesis, in particular pneumoconiosis that is a member selected from the group consisting of aluminosis or bauxite workers' disease, anthracosis or miners' asthma, asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma and talc pneumoconiosis;

bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or *streptococcal* bronchitis and vesicular bronchitis, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis, seasonal allergic rhinitis or perennial allergic rhinitis or sinusitis of whatever type, etiology, or pathogenesis, in particular sinusitis that is a member selected from the group consisting of purulent or nonpurulent sinusitis, acute or chronic sinusitis and ethmoid, frontal, maxillary, or sphenoid sinusitis, rheumatoid arthritis of whatever type, etiology, or pathogenesis, in particular rheumatoid arthritis that is a member selected from the group consisting of acute arthritis, acute gouty arthritis, chronic inflammatory arthritis, degenerative arthritis, infectious arthritis, Lyme arthritis, proliferative arthritis, psoriatic arthritis and vertebral arthritis, gout, and fever and pain associated with inflammation, an eosinophil-related disorder of whatever type, etiology, or pathogenesis, in particular an eosinophil-related disorder that is a member selected from the group consisting of eosinophilia, pulmonary infiltration eosinophilia, Loffler's syndrome, chronic eosinophilic pneumonia, tropical pulmonary eosinophilia, bronchopneumonic aspergillosis, aspergilloma, granulomas containing eosinophils, allergic granulomatous angiitis or Churg-Strauss syndrome, polyarteritis nodosa (PAN) and systemic necrotizing vasculitis, atopic dermatitis, allergic dermatitis, contact dermatitis, or allergic or atopic eczema, urticaria of whatever type, etiology, or pathogenesis, in particular urticaria that is a member selected from the group consisting of immune-mediated urticaria, complement-mediated urticaria, urticariogenic material-induced urticaria, physical agent-induced urticaria, stress-induced urticaria, idiopathic urticaria, acute urticaria, chronic urticaria, angioedema, cholinergic urticaria, cold urticaria in the autosomal dominant form or in the acquired form, contact urticaria, giant urticaria and papular urticaria, conjunctivitis of whatever type, etiology, or pathogenesis, in particular conjunctivitis that is a member selected from the group consisting of actinic conjunctivitis, acute catarrhal conjunctivitis, acute contagious conjunctivitis, allergic conjunctivitis, atopic conjunctivitis, chronic catarrhal conjunctivitis, purulent conjunctivitis and vernal conjunctivitis, uveitis of whatever type, etiology, or pathogenesis, in particular uveitis that is a member selected from the group consisting of inflammation of all or part of the uvea, anterior uveitis, iritis, cyclitis, iridocyclitis, granulomatous uveitis, nongranulomatous uveitis, phacoantigenic uveitis, posterior uveitis, choroiditis; and chorioretinitis, psoriasis;

multiple sclerosis of whatever type, etiology, or pathogenesis, in particular multiple sclerosis that is a member selected from the group consisting of primary progressive multiple sclerosis and relapsing remitting multiple sclerosis, autoimmune/inflammatory diseases of whatever type, etiology, or pathogenesis, in particular an autoimmune/inflammatory disease that is a member selected from the group consisting of autoimmune hematological disorders, hemolytic anemia, aplastic anemia, pure red cell anemia, idiopathic thrombocytopenic purpura, systemic lupus erythematosus, polychondritis, scleroderma, Wegner's granulomatosis, dermatomyositis, chronic active hepatitis, myasthenia gravis, Stevens-Johnson syndrome, idiopathic sprue, autoimmune inflammatory bowel diseases, ulcerative colitis, endocrin opthamopathy, Grave's disease, sarcoidosis, alveolitis, chronic hypersensitivity pneumonitis, primary biliary cirrhosis, juvenile diabetes or diabetes mellitus type I, keratoconjunctivitis sicca, epidemic keratoconjunctivitis, diffuse interstitial pulmonary fibrosis or interstitial lung fibrosis, idiopathic pulmonary fibrosis, cystic fibrosis, glomerulonephritis with and without nephrotic syndrome, acute glomerulonephritis, idiopathic nephrotic syndrome, minimal change nephropathy, inflammatory/hyperproliferative skin diseases, benign familial pemphigus, pemphigus erythematosus, pemphigus foliaceus, and pemphigus vulgaris, prevention of allogeneic graft rejection following organ transplantation, inflammatory bowel disease (IBD) of whatever type, etiology, or pathogenesis, in particular inflammatory bowel disease that is a member selected from the group consisting of collagenous colitis, colitis polyposa, transmural colitis, ulcerative colitis and Crohn's disease (CD), septic shock of whatever type, etiology, or pathogenesis, in particular septic shock that is a member selected from the group consisting of renal failure, acute renal failure, cachexia, malarial cachexia, hypophysial cachexia, uremic cachexia, cardiac cachexia, cachexia suprarenalis or Addison's disease, cancerous cachexia and cachexia as a consequence of infection by the human immunodeficiency virus (HIV), liver injury, pulmonary hypertension of whatever type, etiology or pathogenesis including primary pulmonary hypertension/essential hypertension, pulmonary hypertension secondary to congestive heart failure, pulmonary hypertension secondary to chronic obstructive pulmonary disease, pulmonary venous hypertension, pulmonary arterial hypertension and hypoxia-induced pulmonary hypertension, bone loss diseases, primary osteoporosis and secondary osteoporosis, central nervous system disorders of whatever type, etiology, or pathogenesis, in particular a central nervous system disorder that is a member selected from the group consisting of depression, Alzheimers disease, Parkinson's disease, learning and memory impairment, tardive dyskinesia, drug dependence, arteriosclerotic dementia and dementias that accompany Huntington's chorea, Wilson's disease, paralysis agitans, and thalamic atrophies, infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3, cytomegalovirus (CMV), influenza, adenoviruses and Herpes viruses including *Herpes zoster* and *Herpes simplex*, yeast and fungus infections wherein said yeast and fungi are sensitive to upregulation by TNF-α or elicit TNF-α production in their host, e.g., fungal meningitis, particularly when administered in conjunction with other drugs of choice for the treatment of systemic yeast and fungus infections, including but are not limited to, polymixins, e.g. Polymycin B, imidazoles, e.g. clotrimazole, econazole, miconazole, and ketoconazole, triazoles, e.g. fluconazole and itranazole as well as amphotericins, e.g. Amphotericin B and liposomal Amphotericin B, ischemia-reperfusion injury, ischemic heart disease, autoimmune diabetes, retinal autoimmunity, chronic lymphocytic leukemia, HIV infections, lupus erythematosus, kidney and ureter disease, urogenital and gastrointestinal disorders and prostate diseases, reduction of scar formation in the human or animal body, such as scar formation in the healing of acute wounds, and psoriasis, other dermatological and cosmetic uses, including antiphlogistic, skin-softening, skin elasticity and moisture-increasing activities.

According to one aspect the present invention relates in particular to the treatment of a respiratory disease, such as adult respiratory distress syndrome (ARDS), bronchitis, chronic obstructive pulmonary disease (COPD), cystic fibrosis, asthma, emphysema, bronchiectasis, chronic sinusitis and rhinitis.

According to another aspect the present invention relates in particular to the treatment of gastrointestinal (GI) disorders, in particular inflammatory bowel diseases (IBD) such as Crohn's disease, ileitis, collagenous colitis, colitis polyposa, transmural colitis and ulcerative colitis.

According to a further aspect the present invention relates also to the reduction of scars formation.

A still further aspect of the present invention also relates to the use of the nicotinamide derivatives of formula (I), their pharmaceutically acceptable salts and/or derived forms, for the manufacture of a drug having a PDE4 inhibitory activity. In particular, the present inventions concerns the use of the nicotinamide derivatives of formula (I), their pharmaceutically acceptable salts and/or derived forms, for the manufacture of a drug for the treatment of inflammatory, respiratory, allergic and scar-forming diseases, disorders, and conditions, and more precisely for the treatment of diseases, disorders, and conditions that are listed above.

As a consequence, the present invention provides a particularly interesting method of treatment of a mammal, including a human being, with a PDE4 inhibitor including treating said mammal with an effective amount of a nicotinamide derivative of formula (I), its pharmaceutically acceptable salts and/or derived forms. More precisely, the present invention provides a particularly interesting method of treatment of a mammal, including a human being, to treat an inflammatory, respiratory, allergic and scar-forming disease, disorder or condition, including treating said mammal with an effective amount of a nicotinamide derivative of formula (I), its pharmaceutically acceptable salts and/or derived forms.

The following examples illustrate the preparation of the nicotinamide derivatives of the formula (I):

Where Preparations or Examples are described as being effected by a method "similar to" another method this means that minor differences in the practical method may exist, such as for example use of recrystallisation rather than column chromatography in the purification stage or use of alternative solvents in separation phase. However such minor differences are considered to be within the common general knowledge and experimental experience of the skilled chemist when approaching such reactions.

Preparation 1

2-Chloro-5-fluoro nicotinic acid

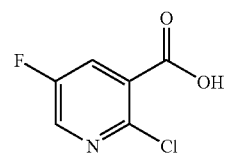

Ethyl-2-chloro-5-fluoro-nicotinoate (50.4 g, 0.247 mol) (prepared according to the method of J. Med. Chem., 1993, 36(18), 2676–88, page 2684, column 2, 3$^{rd}$ example, ethyl-2-chloro-5-fluoropyridine-3-carboxylate) was dissolved in tetrahydrofuran (350 mL) and a 2M aqueous solution of lithium hydroxide (247 mL, 0.495 mol) added. The reaction mixture was stirred at room temperature for 3 days. The pH of the solution was reduced to pH 1 by addition of 6M hydrochloric acid and then extracted with dichloromethane (×3). The combined extracts were dried over magnesium sulphate and the solvent concentrated in vacuo to give a solid which was triturated with diethyl ether and then dried to give the title compound as a white solid, 40.56 g.

$^1$HNMR (DMSO-D$_6$, 400 MHz): 8.20 (s, 1H), 8.62 (s, 1H).

MS ES+ m/z 174 [MH]$^+$

Preparation 2

2-Chloro-5-methyl-nicotinic acid

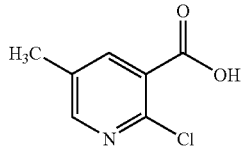

A 2.5M solution of butyllithium in hexane (9.4 mL, 23.5 mmol) was added to tetrahydrofuran (50 mL) and the mixture cooled to −78° C. The mixture was treated with 2,2,6,6-tetramethylpiperidine (4.4 mL, 26.0 mmol) and stirred at −78° C. for 30 minutes. The reaction mixture was then treated with 2-chloro-5-methylpyridine (3.00 g, 23.5 mmol) and stirred at −78° C. for a further 2.5 hours. The reaction mixture was poured into a beaker of dry ice and warmed to room temperature on a water bath, then extracted into water. The mixture was acidified with 2M hydrochloric acid, extracted into ether and washed with water (×2) and brine. The solution was dried over magnesium sulphate to yield the title product as a yellow solid, 1.65 g.

$^1$HNMR (CDCl$_3$, 400 MHz): 2.35(s, 3H), 8.13(m, 1H), 8.42(m, 1H).

MS ES+ m/z 172 [MH]$^+$

Preparation 3

Syn-tert-Butyl 4-aminocyclohexylcarbamate

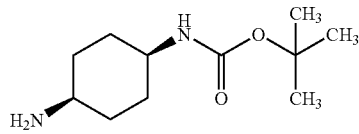

5% Palladium on charcoal (5 g) was mixed with toluene (10 mL) and was added to syn-(4-azido-cyclohexyl)-carbamic acid tert-butyl ester (170 g, 0.71 mol) (prepared according to the method of WO 99/54284, page 80, prep 77(1), cis-4-(N-tert-Butoxycarbonylamino)cyclohexyl azide) in methanol (400 mL). The mixture was hydrogenated (80 atmospheres) at room temperature for 18 hours and then filtered. The solvent was evaporated in-vacuo and the residue was triturated with ethyl acetate (50 mL) and then with hexane (200 mL). The solid obtained was isolated by filtration, dissolved in ethyl acetate (600 mL) and filtered through Celite®. The filtrate was concentrated in-vacuo to give a slush that was diluted with hexane (300 mL). The solid obtained was isolated by filtration and was washed with ethyl acetate in hexane (20:80). The mother liquors were combined and evaporated in-vacuo, the residue was purified by chromatography on silica gel using ethyl acetate and then methanol as eluant. The material obtained was crystallised from ethyl acetate and hexane and combined with the first crop to give the title compound as a white solid, 76.0 g.

Mpt 88–90° C.

$^1$HNMR (CDCl$_3$, 400 MHz): 1.41(s, 9H), 1.52–1.77(m, 8H), 1.82(m, 1H), 1.97(m, 1H), 2.61(m, 1H), 3.62(m, 1H), 4.59(m, 1H).

MS ES+ m/z 215 [MH]$^+$

Preparation 4

1-Fluoro-4-methoxy-2-methylsulfanyl-benzene

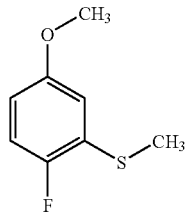

1,2-Difluoro-4-methoxy-benzene (100 mg, 0.69 mmol) and sodium methanethiolate (148 mg, 2.08 mmol) were dissolved in N,N-dimethylformamide (2 mL) and the reaction mixture stirred at 60° C. for 18 hours. Additional sodium methanethiolate (99 mg, 139 mmol) was added and the reaction mixture heated to 100° C. for 18 hours. The reaction mixture was diluted with water and extracted with ether (×2). The ether extracts were washed with water (×2), dried over magnesium sulphate and concentrated in vacuo. The residue was taken up in pentane:ether 1:1 mixture (2 mL) and filtered through a plug of silica in a pipette, washing through with pentane:ether 1:1 mixture (5 mL). The reaction mixture was concentrated in vacuo to yield the title product as a colourless oil, 135 mg.

$^1$HNMR (CDCl$_3$, 300 MHz): 2.45(s, 3H), 3.80(s, 3H), 6.65(dd, 1H), 6.80(dd, 1H), 6.95(t, 1H).

Preparation 5

4-Fluoro-3-methylsulfanyl-phenol

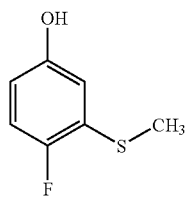

Boron tribromide (2.5 mL, 2.5 mmol) was added to a solution of the ether of preparation 4 (118.3 mg, 0.69 mmol) in dichloromethane (10 mL) at 0° C. under nitrogen and the reaction mixture was stirred at 0° C. for 4 hours. The reaction mixture was then stirred for a further 18 hours at room temperature. The reaction mixture was quenched with sodium carbonate solution (10 mL) and stirred for 1 hour. The mixture was then acidified with 2M hydrochloric acid, the layers separated and the organic phase concentrated in vacuo. The crude product was taken up in a mixture of ether:pentane 1:1 (2 mL) and the solution filtered through a plug of silica in a pipette. The residue was washed with additional ether:pentane 1:1 (5 mL) and concentrated in vacuo to yield the title product as a yellow oil, 110 mg.

$^1$HNMR (CDCl$_3$, 400 MHz): 2.45 (s, 3H), 6.57 (m, 1H), 6.72 (m, 1H), 6.90 (t, 1H).

MS ES− m/z 157 [M−H]$^-$

Preparation 6

5-Isopropyl-1H-pyrazole-3-carboxylic acid ethyl ester

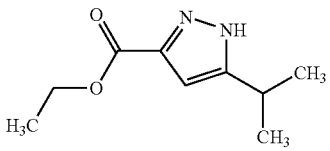

5-Isopropyl-1H-pyrazole-3-carboxylic acid (WO 03/035065, page. 485, example 17b) (1.00 g, 6.49 mmol) was dissolved in a mixture of concentrated sulphuric acid (1.5 mL) and ethanol (25 mL) and the reaction mixture heated at reflux for 3 hours. The reaction mixture was cooled, poured into water, basified with 0.88 ammonia then extracted with ethyl acetate. The ethyl acetate was washed with brine, dried over magnesium sulphate and concentrated in vacuo to yield the title product, 514 mg (43%).

$^1$HNMR (CDCl$_3$, 400 MHz): 1.30(d, 6H), 1.38(t, 3H), 3.64(m, 1H), 4.38(m, 2H), 6.63(s, 1H).

Preparations 7 to 13

Potassium carbonate (2 eq) and potassium iodide, (0.1 eq) were added to a solution of the appropriate phenol (1 eq) in acetonitrile (1.25 mLmmol$^{-1}$), and the mixture warmed to 90° C. 2-(2-Bromoethoxy)tetrahydro-2H-pyran (1.3 eq) was added and the reaction stirred at 90° C. for 72 hours. The cooled reaction mixture was concentrated in vacuo and the residue partitioned between ethyl acetate and 10% citric acid solution, and the layers separated. The organic phase was washed with water, sodium bicarbonate solution and brine, then dried over magnesium sulphate and concentrated in vacuo. The crude product was purified by column chromatography on silica gel using an elution gradient of ethyl acetate:pentane (5:95 to 50:50) to yield the appropriate product.

| No. | Structure | Yield (%) | Data |
|---|---|---|---|
| 7 | | 79 | $^1$HNMR (CDCl$_3$, 400 MHz): 1.50–1.90 (m, 6H), 3.50 (m, 1H), 3.90 (m, 5H), 4.10 (m, 1H), 4.20 (m, 2H), 4.70 (t, 1H), 7.10 (m, 1H), 7.50 (dd, 1H), 7.70 (dd, 1H). MS ES+ m/z 337 [MNa]$^+$ |
| 8 | | 72 | $^1$HNMR (CDCl$_3$, 400 MHz): 1.44–1.90 (m, 6H), 3.54 (m, 1H), 3.80–3.96 (m, 5H), 4.06 (m, 1H), 4.24 (m, 2H), 4.74 (m, 1H), 6.96 (m, 1H), 7.04 (d, 1H), 7.74 (d, 1H). MS ES+ m/z 337 [MNa]$^+$ |
| 9 | | 84 | $^1$HNMR (CDCl$_3$, 400 MHz): 1.46–1.90 (m, 6H), 3.50 (m, 1H), 3.80–3.94 (m, 5H), 4.06 (m, 1H), 4.20 (m, 2H), 4.74 (m, 1H), 6.96 (d, 1H), 7.38 (m, 1H), 7.74 (d, 1H). MS ES+ m/z 337 [MNa]$^+$ |
| 10 | | 72 | $^1$HNMR (CDCl$_3$, 400 MHz): 1.44–1.89 (m, 8H), 2.34 (s, 3H), 3.58 (m, 2H), 3.86 (s, 3H), 4.08 (m, 2H), 4.69 (m, 1H), 7.02 (m, 1H), 7.34 (m, 1H), 7.62 (m, 1H). MS ES+ m/z 317 [MNa]$^+$ |

-continued

| No. | | Yield (%) | Data |
|---|---|---|---|
| 11 | (structure) | 46 | ¹HNMR (CDCl₃, 400 MHz): 1.48–1.92 (m, 6H), 2.38 (m, 3H), 3.54 (m, 1H), 3.80–3.94 (m, 5H), 4.06 (m, 1H), 4.22 (m, 2H), 4.76 (m, 1H), 6.80 (m, 2H), 7.70 (d, 1H). MS ES+ m/z 317 [MNa]⁺ |
| 12 | (structure) | 57 | ¹HNMR (CDCl₃, 400 MHz): 1.44–1.90 (m, 6H), 2.30 (m, 3H), 3.54 (m, 1H), 3.80–3.94 (m, 5H), 4.06 (m, 1H), 4.20 (m, 2H), 4.76 (m, 1H), 6.92 (d, 1H), 7.24 (m, 1H), 7.58 (m, 1H) MS ES+ m/z 317 [MNa]⁺ |
| 13 | (structure) | 80 | ¹HNMR (CDCl₃, 400 MHz): 1.50–1.90 (m, 6H), 2.50 (t, 1H), 3.90 (m, 5H), 4.10 (m, 1H), 4.25 (m, 2H), 4.80 (m, 1H), 7.00 (m, 2H), 7.40 (dd, 1H), 7.80 (dd, 1H). MS ES+ m/z 303 [MNa]⁺ |

In Preparation 7, methyl 3-chlorosalicylate (prepared according to the method of U.S. Pat. No. 4,895,860, page 14, column 2) was used as the starting alcohol.

In Preparation 8, methyl 4-chloro-2-hydroxybenzoate (prepared according to the method of EP 0234872, page 28, synthesis example (2f)) was used as the starting alcohol.

In Preparation 9, methyl 5-chloro-2-hydroxybenzoate (prepared according to the method of EP 0234872, page 28, synthesis example (2c)) was used as the starting alcohol.

In Preparation 10, methyl 2-hydroxy-3-methylbenzoate was used as the starting alcohol.

In Preparation 11, methyl 2-hydroxy-4-methylbenzoate was used as the starting alcohol.

In Preparation 12, methyl 2-hydroxy-5-methylbenzoate was used as the starting alcohol.

In Preparation 13, methyl salicylate was used as the starting alcohol.

Preparation 14

5-Isopropyl-1-[2-(tetrahydro-pyran-2-yloxy)-ethyl]-1H-pyrazole-3-carboxylic acid ethyl ester

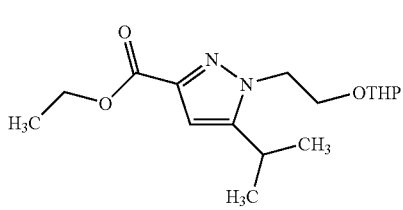

The ester of preparation 6 (509 mg, 2.8 mmol), 2-(2-bromoethoxy)tetrahydro-2H-pyran (732 mg, 3.5 mmol) and potassium carbonate (483 mg, 3.5 mmol) were dissolved in 1-methyl-2-pyrrolidinone (5 mL) and the reaction mixture heated to is 80° C. for 18 hours. The reaction mixture was cooled, poured into ethyl acetate, washed with water (×2) and brine, dried over magnesium sulphate and concentrated in vacuo. The residue was purified by column chromatography on silica gel eluting with pentane:ethyl acetate 80:20 to 60:40 to yield the title product, 663 mg (76%).

¹HNMR (CDCl₃, 400 MHz): 1.25(d, 6H), 1.37(t, 3H), 1.44–1.71(m, 6H), 2.97(m, 1H), 3.42(m, 1H), 3.54(m, 1H), 3.75(m, 1H), 4.00(m, 1H), 4.32(m, 2H), 4.54(t, 1H), 4.68(m, 1H), 4.76(m, 1H), 6.64(s, 1H).

MS ES+ m/z 227 [MH]⁺

Preparation 15

1-[2-(Tetrahydro-pyran-2-yloxy)-ethyl]-1H-imidazole-4-carboxylic acid methyl ester

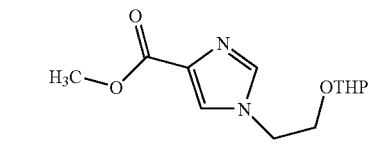

Imidazole-4-carboxylic acid methyl ester (756 mg, 6 mmol) was added slowly to a stirred suspension of sodium hydride (248 mg, 6.2 mmol) in tetrahydrofuran (10 mL) under nitrogen. The reaction mixture was stirred at room temperature for 30 minutes before being treated dropwise with 2-(2-bromoethoxy)-tetrahydro-2H-pyran (1.34 g, 6.4 mmol) and lithium iodide (40 mg, 0.3 mmol). The reaction mixture was allowed to stir at room temperature under nitrogen for 72 hours and then at reflux for 24 hours. The reaction mixture was cooled and diluted with a mixture of ethyl acetate:water 1:1 (300 mL). The aqueous layer was separated and extracted with ethyl acetate (2×50 mL). The organics were combined, dried over magnesium sulphate and concentrated in vacuo. The residue was purified by column chromatography on silica gel eluting with dichloromethane:methanol 100:0 to 98:2 to 96:4 to yield the title product.

$^1$HNMR(CDCl$_3$, 400 MHz): 1.43–1.85(m, 6H), 3.46(m, 1H), 3.60(m, 2H), 3.90(s, 3H), 4.00(m, 1H), 4.18(m, 2H), 4.57(t, 1H), 7.55(s, 1H), 7.65(s, 1H).

MS ES+ m/z 227 [MNa]$^+$

Preparation 16

3-[2-(Tetrahydro-pyran-2-yloxy)-ethyl]-3H-imidazole-4-carboxylic acid methyl ester

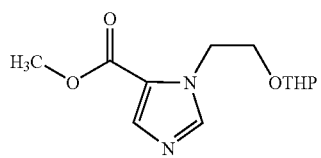

The title compound was prepared by a method similar to that described for preparation 15, however the crude product was purified by column chromatography on silica gel twice eluting with dichloromethane:methanol 200:1 to 100:1 to 50:1 to 25:1. The product of both columns were combined and purified by column chromatography on silica gel eluting with cyclohexane:ethyl acetate:methanol 50:50:1 to 50:50:2 to 50:50:4 to yield the title product.

$^1$HNMR(CDCl$_3$, 400 MHz): 1.42–1.80(m, 6H), 3.42(m, 1H), 3.52(m, 1H), 3.65(m, 1H), 3.83(s, 3H), 4.00(m, 1H), 4.52(m, 3H), 7.73(s, 1H), 7.74(s, 1H).

MS ES+ m/z 277 [MNa]$^+$

Preparation 17

1-[2-(Tetrahydro-pyran-2-yloxy)-ethyl]-1H-pyrazole-3-carboxylic acid ethyl ester

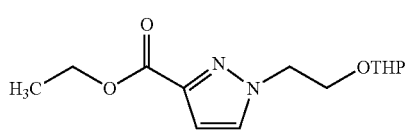

The title compound was prepared by a method similar to that described for preparation 15 using ethyl-pyrazole-3-carboxylate. The crude product was purified by column chromatography on silica gel eluting with dichloromethane:methanol 100:1 to 50:1 to 25:1 to yield the title product.

$^1$HNMR (CDCl$_3$, 400 MHz): 1.37–1.81(m, 12H), 3.42 (dd, 1H), 3.63(dd, 1H), 3.79(m, 1H), 4.08(m, 1H), 4.40(m, 1H), 4.56(m, 1H), 6.81(m, 1H), 7.49(m, 1H).

Preparation 18

2-[2-(Tetrahydro-pyran-2-yloxy)-ethyl]-2H-pyrazole-3-carboxylic acid ethyl ester

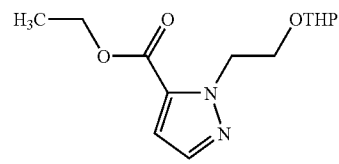

Ethyl-pyrazole-3-carboxylate (980 mg, 7.0 mmol), 2-(2-bromoethoxy)-tetrahydro-2H-pyran (1.57 g, 7.5 mmol), potassium carbonate (1.01 g, 7.3 mmol) and lithium iodide (46.8 mg, 0.35 mmol) were dissolved in 1-methyl-2-pyrrolidinone (10 mL) and the reaction mixture heated to 80° C. for 24 hours. The reaction mixture was allowed to cool for 17 hours and then diluted with a mixture of ethyl acetate:water 1:1 (500 mL). The organic layer was washed with water (3×250 mL), dried over magnesium sulphate and concentrated in vacuo. The residue was purified by column chromatography on silica gel eluting with cyclohexane:ethyl acetate 90:10 to 80:20 to 75:25 to 50:50. The appropriate fractions were combined and concentrated in vacuo to yield the title product.

$^1$HNMR(CDCl$_3$, 400 MHz): 1.40(t, 3H), 1.42–1.80(m, 6H), 3.43(m, 1H), 3.60(m, 1H), 3.78(m, 1H), 4.04(m, 1H), 4.35(q, 2H), 4.55(m, 1H), 4.82(m, 2H), 6.81(m, 1H), 7.48 (m, 1H).

MS ES+ m/z 291 [MNa]$^+$

Preparation 19

1-[2-(Tetrahydro-pyran-2-yloxy)-ethyl]-1H-pyrazole-4-carboxylic acid ethyl ester

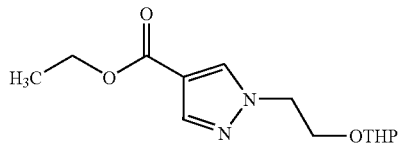

The title compound was prepared by a method similar to that described for preparation 18 using ethyl-pyrazole-4-carboxylate.

$^1$HNMR(CDCl$_3$, 400 MHz): 1.35(t, 3H), 1.43–1.82(m, 6H), 3.48(m, 1H), 3.64(m, 1H), 3.79(m, 1H), 4.13(m, 1H), 4.30(m, 4H), 4.55(m, 1H), 7.90(s, 1H), 7.99(s, 1H).

MS ES+ m/z 291 [MNa]$^+$

Preparation 20

5-Methyl-1-[2-(tetrahydro-pyran-2-yloxy)-ethyl]-1H-pyrazole-3-carboxylic acid ethyl ester

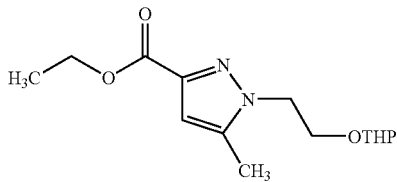

A solution of sodium hydride (934 mg, 23.4 mmol) in tetrahydrofuran (50 mL) was treated with ethyl 3-methylpyrazole-5-carboxylate (3.00 g, 19.5 mmol) and the reaction mixture stirred at room temperature for 30 minutes. 2-(2-Bromoethoxy)tetrahydro-2H-pyran (3.5 mL, 19.5 mmol) and lithium iodide (50 mg, 0.39 mmol) were added and the reaction mixture refluxed for 16 hours. The reaction mixture was cooled and taken up in ethyl acetate and water. The organics were separated and washed with 10% citric acid solution, water, saturated sodium hydrogencarbonate solution and brine, dried over magnesium sulphate and concentrated in vacuo. The residue was purified by column chromatography on silica gel eluting with dichloromethane:methanol 99:1 to 95:5 to yield the title product, 4.47 g.

¹HNMR (CDCl₃, 400 MHz): 1.36(t, 3H), 1.42–1.77(m, 6H), 2.37(s, 3H), 3.41(m, 1H), 3.58(m, 1H), 3.77(m, 1H), 4.03(m, 1H), 4.30(m, 2H), 4.40(m, 2H), 4.47(m, 1H), 6.49 (m, 1H).
MS ES+ m/z 283 [MH]⁺

Preparation 21

5-Ethyl-1-[2-(tetrahydro-pyran-2-yloxy)-ethyl]-1H-pyrazole-3-carboxylic acid methyl ester

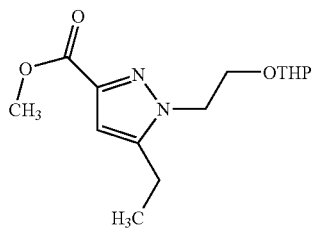

2,2-Dimethoxy-butane (50.0 g, 423 mmol) and pyridine (68.4 mL, 846 mmol) were dissolved in dichloromethane (250 mL) and the solution treated dropwise with trichloroacetyl chloride (94.4 mL, 846 mmol). The reaction mixture was stirred at 30° C. for 18 hours and was then allowed to cool to room temperature. The reaction mixture was diluted with 0.5M hydrochloric acid (362 mL) an stirred for 30 minutes. The organic phase was separated and washed with water (350 mL), dried over magnesium sulphate and concentrated in vacuo. The residue was dissolved in methanol (250 mL) and treated dropwise with a 90% solution of 2-hydroxyethyl hydrazine in methanol (32 mL). The reaction mixture was the refluxed for 18 hours, allowed to cool and concentrated in vacuo. The residue was purified by column chromatography on silica gel eluting with hexane:ethyl acetate 66:33 to 0:100 and the required product isolated. The product (100.0 g, 504 mmol) was dissolved in dichloromethane (1000 mL) and the solution treated with 3,4-dihydro-2H-pyran (68.7 mL, 756 mmol). The solution was warmed to 30° C. and a catalytic amount of bis (trimethylsilyl) sulphate added. The reaction mixture was stirred for 48 hours at 30° C. and then treated with pyridine (20 mL) and stirred for an additional hour. The reaction mixture was concentrated in vacuo and the residue purified by column chromatography on silica gel eluting with hexane:ethyl acetate 66:33 to 33:66 to yield the title product.

¹HNMR(CDCl₃, 400 MHz): 1.22(t, 3H), 1.34–1.67(m, 6H), 2.64(m, 2H), 3.22(m, 1H), 3.40(m, 1H), 3.71(m, 1H), 3.83(s, 3H), 4.02(m, 1H), 4.22(m, 2H), 4.41(m, 1H), 6.61(m, 1H).

Preparations 22 to 31

A mixture of the appropriate ester (1 eq) and a 1M aqueous solution of lithium hydroxide (8–12 mLmmol⁻¹) in tetrahydrofuran (5–11 mLmmol⁻¹) was stirred at room temperature for 72 hours. The reaction mixture was concentrated in vacuo and the residue acidified with 10% aqueous citric acid solution. The aqueous solution was extracted with ethyl acetate, and the combined organic extracts were washed with brine, dried over magnesium sulphate and concentrated in vacuo to yield the appropriate product.

| No. | | Data |
|---|---|---|
| 22 | 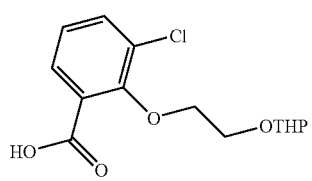 | ¹HNMR (CDCl₃, 400 MHz): 1.46–1.94 (m, 6H), 3.56 (m, 1H), 3.76–3.90 (m, 2H), 4.10 (m, 1H), 4.22 (m, 1H), 4.52 (m, 1H), 4.74 (m, 1H), 7.23 (t, 1H), 7.62 (m, 1H), 8.12 (m, 1H). MS ES+ m/z 323 [MNa]⁺ |

-continued

| No. | | Data |
|---|---|---|
| 23 | 4-Cl, 2-(OCH₂CH₂OTHP) benzoic acid | ¹HNMR (CDCl₃, 400 MHz): 1.40–1.90 (m, 6H), 3.56 (m, 1H), 3.86 (m, 2H), 4.16 (m, 1H), 4.30–4.46 (m, 2H), 4.74 (m, 1H), 7.06 (s, 1H), 7.14 (m, 1H), 8.14 (d, 1H). MS ES+ m/z 323 [MNa]⁺ |
| 24 | 5-Cl, 2-(OCH₂CH₂OTHP) benzoic acid | ¹HNMR (CDCl₃, 400 MHz): 1.48–1.90 (m, 6H), 3.54 (m, 1H), 3.82 (m, 2H), 4.16 (m, 1H), 4.28–4.44 (m, 2H), 4.78 (m, 1H), 7.00 (d, 1H), 7.50 (m, 1H), 8.16 (d, 1H). MS ES+ m/z 323 [MNa]⁺ |
| 25 | 3-CH₃, 2-(OCH₂CH₂OTHP) benzoic acid | ¹HNMR (CDCl₃, 400 MHz): 1.46–1.96 (m, 6H), 2.40 (s, 3H), 3.54 (m, 1H), 3.70–3.90 (m, 2H), 4.10 (m, 1H), 4.18 (m, 2H), 4.74 (m, 1H), 7.20 (m, 1H), 7.44 (d, 1H), 7.92–8.06 (m, 1H). MS ES+ m/z 303 [MNa]⁺ |
| 26 | 4-CH₃, 2-(OCH₂CH₂OTHP) benzoic acid | ¹HNMR (CDCl₃, 400 MHz): 1.44–1.94 (m, 6H), 2.40 (s, 3H), 3.54 (m, 1H), 3.78–3.90 (m, 2H), 4.08–4.20 (m, 1H), 4.32–4.46 (m, 2H), 4.74 (m, 1H), 6.88 (s, 1H), 6.96 (m, 1H), 8.06 (d, 1H). MS ES+ m/z 303 [MNa]⁺ |
| 27 | 5-CH₃, 2-(OCH₂CH₂OTHP) benzoic acid | ¹HNMR (CDCl₃, 400 MHz): 1.44–1.94 (m, 6H), 2.34 (s, 3H), 3.56 (m, 1H), 3.78–3.92 (m, 2H), 4.12 (m, 1H), 4.30–4.44 (m, 2H), 4.72 (m, 1H), 6.96 (d, 1H), 7.34 (m, 1H), 8.00 (s, 1H). MS ES+ m/z 303 [MNa]⁺ |
| 28 | 2-(OCH₂CH₂OTHP) benzoic acid | ¹HNMR (DMSO-D₆, 400 MHz): 1.45 (m, 6H), 1.60 (m, 1H), 1.70 (m, 1H), 3.41 (m, 1H), 3.75 (m, 2H), 3.89 (m, 1H), 4.70 (t, 1H), 7.00 (t, 1H), 7.15 (d, 1H), 7.46 (m, 1H), 7.60 (m, 1H). MS ES− m/z 265 [M − H]⁻ |
| 29 | 1-(CH₂CH₂OTHP)-5-methyl-pyrazole-3-carboxylic acid | ¹HNMR (CDCl₃, 400 MHz): 1.42–1.75 (m, 6H), 2.37 (s, 3H), 3.33 (m, 1H), 3.58 (m, 1H), 3.78 (m, 1H), 4.35 (t, 2H), 4.50 (m, 1H), 6.59 (s, 1H). MS APCl − m/z 253 [M − H]⁻ |

| No. | | Data |
|---|---|---|
| 30 | (structure: 1-[2-(THP-oxy)ethyl]-5-ethyl-pyrazole-3-carboxylic acid) | ¹HNMR (CDCl₃, 400 MHz): 1.27 (t, 3H), 1.41–1.89 (m, 6H), 2.71 (q, 2H), 3.38–3.64 (m, 2H), 3.7–3.85 (m, 1H), 4.30 (t, 2H), 4.48 (s, 1H), 4.93 (s, 1H), 6.73 (s, 1H). MS ES⁺ m/z 291 [MNa]⁺ |
| 31 | (structure: 1-[2-(THP-oxy)ethyl]-5-(1-methylethyl... actually 5-(1-ethyl) pyrazole carboxylic acid) | ¹HNMR (CDCl₃, 400 MHz): 1.28 (m, 6H), 1.46–1.71 (m, 6H), 3.15 (m, 1H), 3.45 (m, 1H), 3.62 (m, 1H), 3.83 (m, 1H), 4.34 (t, 2H), 4.57 (t, 1H), 6.63 (s, 1H). MS APCl+ m/z 299 [MH]⁺ |

Preparation 32

1-[2-(Tetrahydro-pyran-2-yloxy)-ethyl]-1H-imidazole-4-carboxylic acid

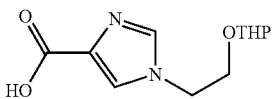

A solution of sodium hydroxide (237 mg, 5.94 mmol) in water (2 mL) was added dropwise to a solution of the ester of preparation 15 (785 mg, 3.08 mmol) in ethanol (8 mL) and the reaction mixture stirred at room temperature for 72 hours. The reaction mixture was acidified to pH 3 with 2M hydrochloric acid and then concentrated in vacuo. The residue was azeotroped with tetrahydrofuran (×3). The crude product was extracted with tetrahydrofuran by trituration at reflux and filtered hot. The solid was recovered and the trituration process repeated. The combined filtrates were concentrated in vacuo and the residue triturated with ether to yield the title product as a white solid, 440 mg.

¹HNMR(DMSO-D₆, 400 MHz): 1.40(m, 4H), 1.60(m, 2H), 3.40(m, 1H), 3.50(m, 1H), 3.65(m, 1H), 3.85(m, 1H), 4.20(m, 2H), 4.57(t, 1H), 7.75(s, 1H), 7.84(s, 1H).

MS ES– m/z 239 [M–H]⁻

The following compounds were prepared by a method similar to that described for preparation 32 using the appropriate ester.

| No | | Data |
|---|---|---|
| 33 | (imidazole-5-carboxylic acid with N-CH₂CH₂-OTHP) | ¹HNMR(DMSO-D₆, 400 MHz): 1.30–1.68(m, 6H), 3.35(m, 2H), 3.61(m, 2H), 4.46(m, 3H), 7.60(s, 1H), 7.94(s, 1H). MS ES– m/z 239 [M – H]⁻ |
| 34 | (pyrazole-3-carboxylic acid with N-CH₂CH₂-OTHP) | ¹HNMR(DMSO-D₆, 400 MHz): 1.40(m, 4H), 1.60(m, 2H), 3.35(m, 1H), 3.48(m, 1H), 3.70(m, 1H), 4.32(m, 2H), 4.51(m, 1H), 6.65(s, 1H), 7.80(s, 1H). MS ES– m/z 239 [M – H]⁻ |
| 35 | (pyrazole-5-carboxylic acid with N-CH₂CH₂-OTHP) | ¹HNMR(DMSO-D₆, 400 MHz): 1.27–1.67(m, 6H), 3.32(m, 1H), 3.45(m, 1H), 3.67(m, 1H), 3.85(m, 1H), 4.46(m, 1H), 4.62(m, 1H), 4.75(m, 1H), 6.79(s, 1H), 7.50(s, 1H). MS ES– m/z 239 [M – H]⁻ |

| No | Data |
|---|---|
| 36 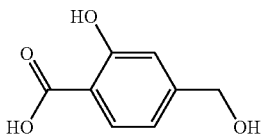 | ¹HNMR(DMSO-D₆, 400 MHz): 1.30–1.68(m, 6H), 3.35(m, 1H), 3.50(m, 1H), 3.72(m, 1H), 3.91(m, 1H), 4.30(m, 2H), 4.52(m, 1H), 7.78(s, 1H), 8.18(s, 1H). MS ES– m/z 239 [M – H]⁻ |

Preparation 37

2-Hydroxy-4-hydroxymethylbenzoic acid

A mixture of 3-hydroxybenzylalcohol (10 g, 80 mmol) and potassium carbonate (33.35 g, 240 mmol) were stirred under carbon dioxide in a sealed vessel at 1500-2000 psi and 150° C. for 18 hours. The cooled residue was dissolved in water, acidified to pH 1 using concentrated hydrochloric acid and extracted with ethyl acetate. The combined organic extracts were washed with brine, dried (MgSO₄) and evaporated under reduced pressure. The product was recrystallised from cyclohexane to afford the title compound, 740 mg.

¹HNMR (CD₃OD, 400 MHz): 4.60(s, 2H), 6.83(m, 1H), 6.92(m, 1H), 7.79(m, 1H).

MS APCI+ m/z 168 [MH]⁺

Preparation 38

5-Fluoro-2-(3-methylsulfanyl-phenoxy)-nicotinic acid ethyl ester

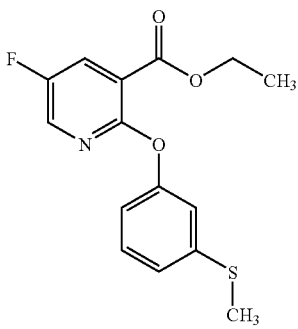

A solution of ethyl-2-chloro-5-fluoro-nicotinoate (50.4 g, 0.247 mol) (prepared according to the method of J. Med. Chem., 1993, 36(18), 2676–88, page 2684, column 2, 3ʳᵈ example, ethyl-2-chloro-5-fluoropyridine-3-carboxylate) (29 g, 0.143 mol) and 3-methylsulphanyl-phenol (20 g, 0.143 mol) (prepared according to the method of WO 98/45268, page 68, preparation 61) in dioxane (300 mL) was treated with caesium carbonate (46.5 g, 0.143 mol) at room temperature. The reaction mixture was heated to 100° C. and stirred for 48 hours. The reaction mixture was concentrated in vacuo and the residue taken up in water (600 mL) and extracted with ethyl acetate (3×250 mL). The organics were combined, washed with brine (200 mL), dried over magnesium sulphate and concentrated in vacuo. The residue was purified by column chromatography on silica gel eluting with dichloromethane:toluene (99.75:0.25 to 99.5:0.5) to yield the title product as a yellow oil, 27.1 g (62%).

¹HNMR(CDCl₃, 400 MHz): 1.37(t, 3H), 2.23(s, 3H), 4.40(q, 2H), 6.84(m, 1H), 7.01(m, 1H) 7.08(m, 1H), 7.26(m, 1H), 7.98(m, 1H), 8.13(m, 1H).

MS APCI+ m/z 308 [MH]⁺

Preparation 39

5-Fluoro-2-(3-methylsulfanyl-phenoxy)-nicotinic acid

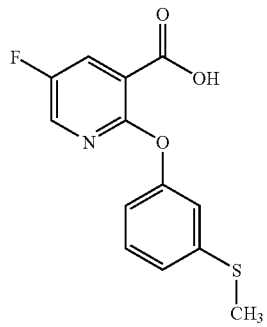

The ester of preparation 38 (27.1 g, 88.2 mmol) was dissolved in tetrahydrofuran (300 mL) and the solution treated with a 1M aqueous solution of lithium hydroxide (220 mL, 220 mmol). The reaction mixture was stirred at room temperature for 2 hours. The reaction mixture was concentrated in vacuo to remove the tetrahydrofuran and the aqueous was cooled to 0° C. before being acidified to pH 1 with hydrochloric acid. The resulting pink precipitate was removed by filtration and washed with iced water. The solid was dissolved in dichloromethane (800 mL) and washed with acidified brine solution (200 mL). The organic layer was separated, dried over magnesium sulphate and concentrated in vacuo. The residue was triturated with toluene to yield the title product as a white solid, 22.13 g (90%).

¹HNMR(CD₃OD, 400 MHz): 2.43(s, 3H), 6.83(m, 1H), 7.01(m, 1H), 7.06(m, 1H), 7.25(m,1H), 8.03(m, 2H).

MS APCI+ m/z 280 [MH]⁺

Preparation 40

Syn-(4-{[5-Fluoro-2-(3-methylsulfanyl-phenoxy)-pyridine-3-carbonyl]-amino}-cyclohexyl)-carbamic acid tert-butyl ester

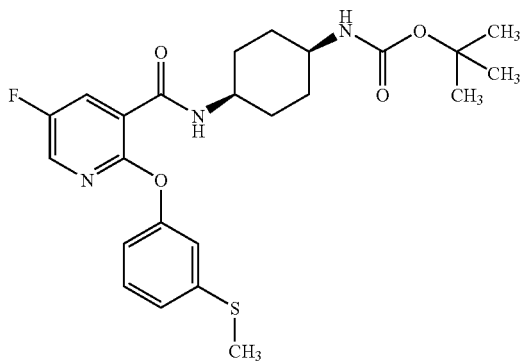

The acid of preparation 39 (5 g, 17.9 mmol) and N,N-dimethylformamide (5 drops) were dissolved in dichloromethane (100 mL) and the reaction mixture cooled to 0° C. The reaction mixture was treated drop-wise with oxalyl chloride (3.1 mL, 35.8 mmol) over 15 minutes and then stirred at room temperature for 2 hours. The reaction mixture was concentrated in vacuo and the residue taken up in dichloromethane (100 mL). The solution was cooled to 0° C. and treated with triethylamine (7.5 mL, 54 mmol) and the amine of preparation 3 (4.2 g, 19.6 mmol). The reaction mixture was allowed to warm to room temperature and was stirred at room temperature for 48 hours. The reaction mixture was diluted with dichloromethane (100 mL) and washed with water (70 mL), 10% citric acid solution (2×70 mL), saturated sodium hydrogencarbonate solution (2×70 mL) and water (70 mL). The organic layer was dried over magnesium sulphate and concentrated in vacuo to yield the title product, 8.0 g.

$^1$HNMR(CDCl$_3$, 400 MHz): 1.40(s, 9H), 1.53(m, 2H), 1.68(m, 2H), 1.77(m, 4H), 2.46(s, 3H), 3.60(m, 1H), 4.18(m, 1H), 4.37(m, 1H), 6.88(m, 1H), 7.02(m, 1H), 7.17(m, 1H), 7.37(m, 1H), 7.93(m, 1H), 8.06(m, 1H), 8.36(m, 1H).

MS ES+ m/z 476 [MH]$^+$

Preparation 41

Syn-N-(4-Amino-cyclohexyl)-5-fluoro-2-(3-methyl-sulfanyl-phenoxy)-nicotinamide hydrochloride

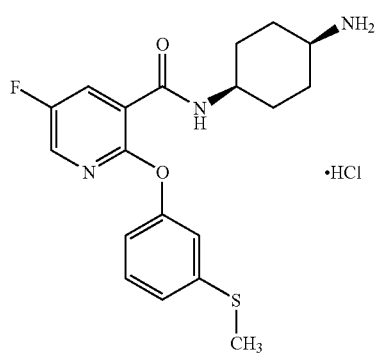

The Boc protected amine of preparation 40 (8.0 g, 16.8 mmol) was dissolved in dioxane (50 mL) and the solution treated with a 4M solution of hydrochloric acid in dioxane (25 mL). The reaction mixture was stirred at room temperature for 5 hours before being concentrated in vacuo and azeotroped with ethyl acetate and dichloromethane to yield the title product, 5.0 g.

$^1$HNMR(CD$_3$OD, 400 MHz): 1.67(m, 2H), 1.80–2.01(m, 6H), 2.45(s, 3H), 3.24(m, 1H), 4.14(m, 1H), 6.92(m, 1H), 7.09(m, 1H), 7.17(m, 1H), 7.35(t, 1H), 8.08(m, 2H).

MS ES+ m/z 376 [MH]$^+$

Preparation 42

Syn-{4-[(2-Chloro-5-fluoro-pyridine-3-carbonyl)-amino]-cyclohexyl}-carbamic acid tert-butyl ester

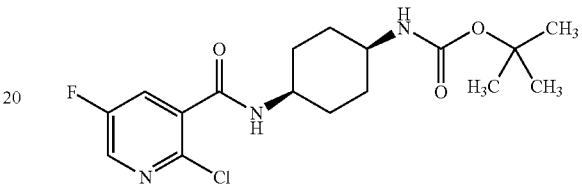

A solution of the acid of preparation 1 (8.75 g, 49 mmol) and N,N-dimethylformamide (5 drops) in dichloromethane (200 mL) was cooled to 0° C. and treated with oxalyl chloride (10.4 mL, 119 mmol) over 10 minutes. The reaction mixture was stirred at room temperature for 18 hours. The reaction mixture, was concentrated in vacuo and the residue azeotroped with dichloromethane (×2). The product was taken up in dichloromethane (200 mL) and the solution treated with N-ethyldiisopropylamine (17.1 mL, 98 mmol) and the amine of preparation 3 (11.55 g, 54 mmol). The reaction mixture was stirred at room temperature for 18 hours and then washed with 10% citric acid solution (×2) and saturated sodium hydrogencarbonate solution (×2). The mixture then was dried over magnesium sulphate and concentrated in vacuo to yield the title product as a yellow solid, 18.02 g (98%).

$^1$HNMR(DMSO-D$_6$, 400 MHz): 1.21(m, 2H), 1.32(s, 9H), 1.51(m, 2H), 1.73–1.88(m, 4H), 2.63(m, 1H), 2.83(m, 1H), 3.60(m, 1H), 6.63(m, 1H), 7.86(m, 1H), 8.44(m, 1H).

MS ES– m/z 370 [M–H]$^-$

Preparation 43

Syn-(4-{[5-Fluoro-2-(3-methylsulfanyl-phenoxy)-pyridine-3-carbonyl]-amino}-cyclohexyl)-carbamic acid tert-butyl ester

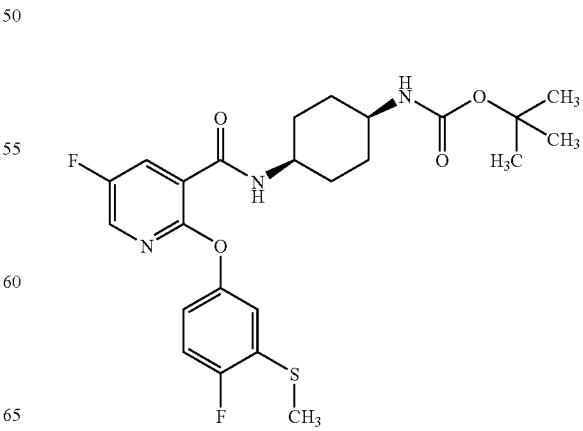

The chloro compound of preparation 42 (6.4 g, 17.2 mmol), the phenol of preparation 5 (3.0 g, 19.0 mmol) and caesium carbonate (11.2 g, 34.4 mmol) were dissolved in dioxane (200 mL) and the reaction mixture refluxed for 72 hours. The reaction mixture was cooled to room temperature and concentrated in vacuo. The residue was taken up in ethyl acetate and water and the layers separated. The aqueous was extracted with ethyl acetate and the organic layers were combined, dried over magnesium sulphate and concentrated in vacuo. The residue was purified by column chromatography on silica gel eluting with dichloromethane:methanol 99.5:0.5 to 99:1 to 98:2 to yield the title product as a pale yellow foam, 6.31 g (74%).

$^1$HNMR (CDCl$_3$, 400 MHz): 1.42–1.84 (m, 17H), 2.48 (s, 3H), 3.62 (m, 1H), 4.18(m, 1H), 4.21 (m, 1H), 6.82 (m, 1H), 7.01 (m, 1H), 7.22 (t, 1H), 7.88 (m, 1H), 8.04 (m, 1H), 8.36 (m, 1H).

MS ES+ m/z 516 [MNa]$^+$

Preparation 44

Syn-N-(4-Amino-cyclohexyl)-5-fluoro-2-(3-methyl-sulfanyl-phenoxy)-nicotinamide hydrochloride

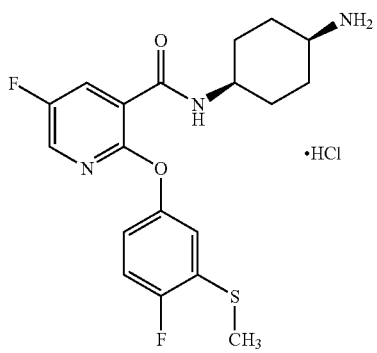

A solution of the Boc protected amine of preparation 43 (6.31 g, 12.8 mmol) was dissolved in dichloromethane (100 mL) and cooled to 0° C. Hydrogen chloride gas was bubbled through the reaction mixture for 1 hour and the mixture was then allowed to stir for a further hour. Hydrogen chloride gas was then again bubbled through the reaction for 1 hour and the reaction mixture allowed to stir at room temperature for 48 hours. The reaction was concentrated in vacuo and the residue was triturated with ethyl acetate to yield the title product as a pale pink solid, 4.70 g.

$^1$HNMR (DMSO-D$_6$, 400 MHz): 1.60–1.84 (m, 8H), 2.45 (s, 3H), 3.11 (m, 1H), 3.92 (m, 1H), 7.03 (m, 1H), 7.22 (m, 2H), 7.92–8.04 (m, 4H), 8.21 (m, 1H), 8.31 (m, 1H).

MS APCI+ m/z 394 [MH]$^+$

Preparation 45

Syn-{4-[(2-Chloro-5-methyl-pyridine-3-carbonyl)-amino]-cyclohexyl}-carbamic acid tert-butyl ester

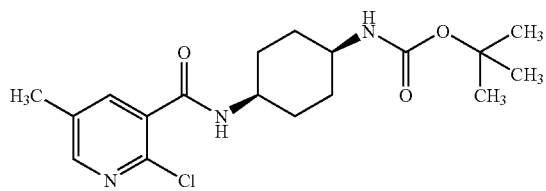

The carboxylic acid of preparation 2 (1.50 g, 8.74 mmol) was dissolved in N,N-dimethylformamide (15 mL) and the solution treated with N,N'-carbonyldiimidazole (1.42 g, 8.74 mmol) and stirred at room temperature for 1 hour. The reaction mixture was treated with the amine of preparation 3 (2.10 g, 9.63 mmol) and stirred at room temperature for 72 hours. The reaction mixture was concentrated in vacuo and the residue taken up in 10% citric acid solution and ether. The organic layer was separated and washed with 10% citric acid solution, water, saturated sodium hydrogencarbonate solution and brine. The organic layer was then dried over magnesium sulphate and concentrated in vacuo to yield the title product as a white foam, 3.61 g.

$^1$HNMR(CDCl$_3$, 400 MHz): 1.44(s, 9H), 1.61–1.93(m, 8H), 2.36(s, 3H), 3.62(m, 1H), 4.18(m, 1H), 4.54(m, 1H), 6.57(m, 1H), 7.96(m, 1H), 8.27(m, 1H).

MS ES+ m/z 288 [MH]$^+$

Preparation 46

Syn-{4-[(2,5-Dichloro-pyridine-3-carbonyl)-amino]-cyclohexyl}-carbamic acid tert-butyl ester

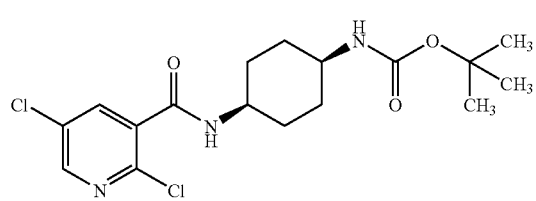

The title compound was prepared by a method similar to that described in preparation 45 using 2,5-dichloronicotinic acid (prepared according to the method of WO 95/30676, page 19, Method 1(b)) and the amine of preparation 4.

$^1$HNMR(CDCl$_3$, 400 MHz): 1.41(s, 9H), 1.46–1.66(m, 4H), 1.80–1.93(m, 4H), 3.63(m, 1H), 4.15(m, 1H), 4.52(m, 1H), 6.54(m, 1H), 8.13(m, 1H), 8.40(m, 1H).

MS ES+ m/z 288 [MH]$^+$

Preparation 47

Syn-(4-{[5-Methyl-2-(3-methylsulfanyl-phenoxy)-pyridine-3-carbonyl]-amino}-cyclohexyl)-carbamic acid tert-butyl ester

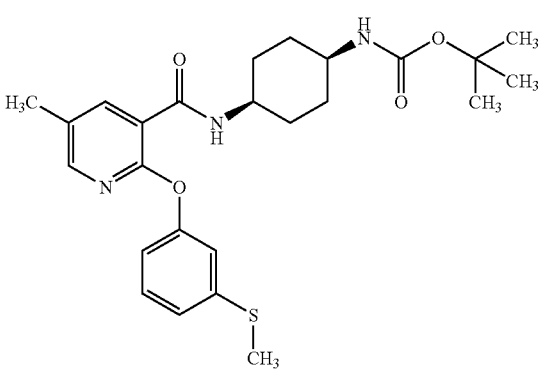

The chloro compound of preparation 45 (1.30 g, 3.54 mmol), 3-methylsulphanyl-phenol (prepared according to the method of WO 98/45268, page 68, preparation 61) and caesium carbonate (2.33 g, 7.08 mmol) were dissolved in acetonitrile (25 mL) and the reaction mixture heated to reflux for 24 hours. The reaction mixture was allowed to cool and diluted with ethyl acetate (200 mL) and water (200 mL). The organic layer was separated and washed with 10% citric acid solution (×2), water, 1M lithium hydroxide solution and brine. The organic layer was then dried over magnesium sulphate and concentrated in vacuo. The residue was purified by column chromatography on silica gel eluting with pentane:ethyl acetate 90:10 to 10:90 to yield the title product, 810 mg.

¹HNMR (CDCl₃, 400 MHz): 1.38–1.50 (m, 11H), 1.64–1.83 (m, 6H), 2.34 (s, 3H), 2.49 (s, 3H), 3.60 (m, 1H), 4.19 (m, 1H), 4.39 (m, 1H), 6.87 (m, 1H), 7.01 (s, 1H), 7.14 (d, 1H), 7.34 (t, 1H), 7.81 (m, 1H), 8.02 (s, 1H), 8.41 (s, 1H).
MS APCI+ m/z 472 [MH]+

Preparation 48

Syn-(4-{[5-Chloro-2-(3-methylsulfanyl-phenoxy)-pyridine-3-carbonyl]-amino}-cyclohexyl)-carbamic acid tert-butyl ester

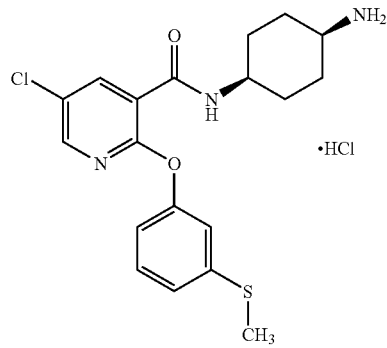

The title compound was prepared by a method similar to that described for preparation 47 using the chloro compound of preparation 46.

¹HNMR (CDCl₃, 400 MHz): 1.42–1.53 (m, 11H), 1.62–1.84 (m, 6H), 2.50 (s, 3H), 3.60 (m, 1H), 4.16 (m, 1H), 4.20 (m, 1H), 6.89 (d, 1H), 7.02 (s, 1H), 7.18 (d, 1H), 7.39 (t, 1H), 7.85 (m, 1H), 8.16 (m, 1H), 8.56 (m, 1H).
MS APCI+ m/z 492 [MH]+

Preparation 49

Syn-N-(4-Amino-cyclohexyl)-5-methyl-2-(3-methyl-sulfanyl-phenoxy)-nicotinamide hydrochloride

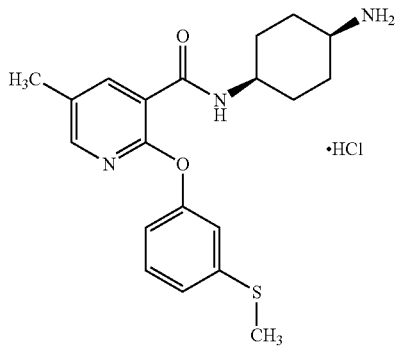

The Boc protected amine of preparation 47 (800 mg, 1.69 mmol) and a 4M solution of hydrochloric acid in dioxan (30 mL) were dissolved in dichloromethane (5 mL) and the reaction mixture stirred at room temperature for 3 hours. The reaction mixture was concentrated in vacuo to yield the title product as a white solid, 600 mg.

¹HNMR (CD₃OD, 400 MHz): 1.60–1.72 (m, 2H), 1.79–1.96 (m, 6H), 2.34 (s, 3H), 2.47 (s, 3H), 3.22 (m, 1H), 4.12 (m, 1H), 6.97 (m, 1H), 7.08 (m, 1H), 7.12 (m, 1H), 7.34 (t, 1H), 8.04 (m, 1H), 8.12 (m, 1H).
MS APCI+ m/z 372 [MH]+

Preparation 50

Syn-N-(4-Amino-cyclohexyl)-5-chloro-2-(3-methyl-sulfanyl-phenoxy)-nicotinamide hydrochloride

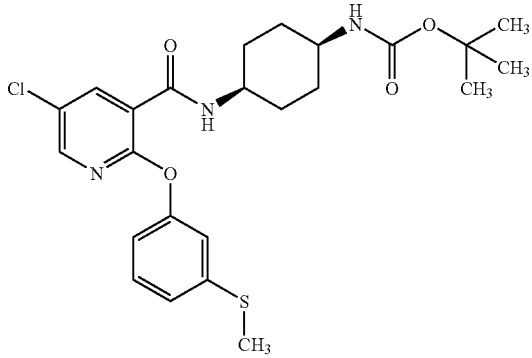

The title compound was prepared by a method similar to that described for preparation 49 using the Boc protected amine of preparation 48.

¹HNMR (CD₃OD, 400 MHz): 1.71(m, 2H), 1.79–2.01(m, 6H), 2.46(s, 3H), 3.27(m, 1H), 4.17(m, 1H), 6.82(m, 2H), 7.09(m, 1H), 7.16(m, 1H), 7.34(t, 2H).
MS APCI+ m/z 392 [MH]+

Preparation 51

Syn-5-Fluoro-2-(4-fluoro-3-methylsulfanyl-phenoxy)-N-(4-{2-[2-(tetrahydro-pyran-2-yloxy)-ethoxy]-benzoylamino}-cyclohexyl)-nicotinamide

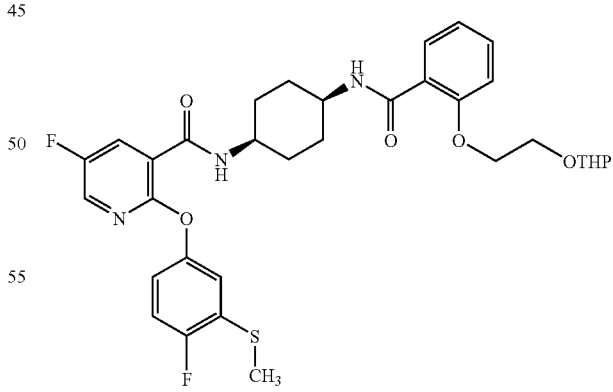

The amine of preparation 44 (150 mg, 0.35 mmol), 1-(3-dimethylaminopropyl)-3-ethylcarbodiimide hydrochloride (87 mg, 0.45 mmol), 1-hydroxybenzotriazole hydrate (69 mg, 0.45 mmol), N-ethyldiisopropylamine (0.24 mL, 1.4 mmol) and the carboxylic acid of preparation 28 (102 mg, 0.38 mmol) were dissolved in dichloromethane (10 mL). The reaction mixture was stirred at room temperature for 18 hours. The reaction mixture was diluted with water and the layers separated by filtration with a phase separation tube. The organic layer was concentrated in vacuo and the crude product purified by column chromatography on silica gel eluting with dichloromethane:methanol 98:2 to yield the title product, 215 mg.

$^1$HNMR (CDCl$_3$, 400 MHz): 1.34–1.96(m, 17H), 2.39(s, 3H), 3.38(m, 1H), 3.65(m, 2H), 3.91(m, 1H), 4.20(m, 2H), 4.44(m, 1H), 5.27(s, 1H), 6.92(d, 1H), 7.06(m, 2H), 7.21(m, 1H), 7.39(m, 1H), 7.92(m, 1H), 8.03(m, 1H), 8.18(m, 1H), 8.35(m, 1H).

MS ES+ m/z 664 [MNa]$^+$

Preparation 52

Syn-5-Fluoro-2-(3-methylsulfanyl-phenoxy)-N-[4-({1-[2-(tetrahydro-pyran-2-yloxy)-ethyl]-1H-imidazole-4-carbonyl}-amino)-cyclohexyl]-nicotinamide

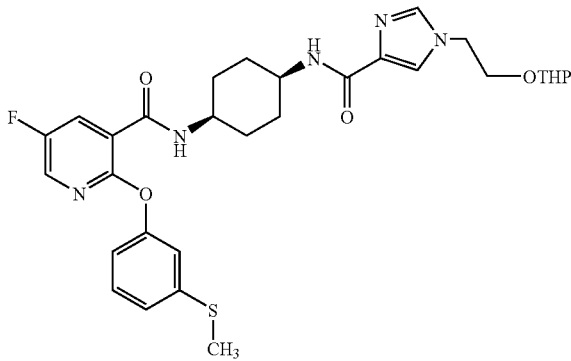

The carboxylic acid of preparation 32 (192 mg, 0.8 mmol) was dissolved in N,N-dimethylformamide (9 mL) and the solution treated with N-ethyldiisopropylamine (361 mg, 2.8 mmol), 1-hydroxybenzotriazole hydrate (124.3 mg, 0.92 mmol) and 1-(3-dimethylaminopropyl)-3-ethylcarbodiimide hydrochloride (199.3 mg, 1.04 mmol).

The reaction mixture was stirred at room temperature for 15 minutes before the amine of preparation 41 (329.5 mg, 0.8 mmol) was added. The reaction mixture was stirred at room temperature for 40 hours, then concentrated in vacuo and the residue partitioned between a mixture of ethyl acetate:water 1:1 (300 mL). The organic layer was washed with water (2×100 mL), 5% sodium carbonate solution (75 mL) and again with water (75 mL). The organic layer was dried over magnesium sulphate and concentrated in vacuo. The residue was purified by column chromatography on silica gel eluting with dichloromethane:ethyl acetate:methanol 90:10:0 to 100:10:2 to 100:10:4. The crude product was azeotroped with dichloromethane to yield the title product as a colourless solid, 408 mg (85%).

$^1$HNMR(CDCl$_3$, 400 MHz): 1.55–1.96(m, 14H), 2.50(s, 3H), 3.48(m, 1H), 3.64(m, 2H), 4.12(m, 2H), 4.20(m, 1H), 4.55(m, 1H), 6.90(m, 1H), 6.98(m, 1H), 7.02(s, 1H), 7.16(d, 1H), 7.36(t, 1H), 7.45(s, 1H), 7.60s, 1H), 7.95(m, 1H), 8.05(d, 1H), 8.35(d, 1H).

MS ES+ m/z 620 [MNa]$^+$

The following compounds, of the general formula shown below, were prepared by a method similar to that described for preparation 53 using the appropriate carboxylic acid (R$^3$COOH).

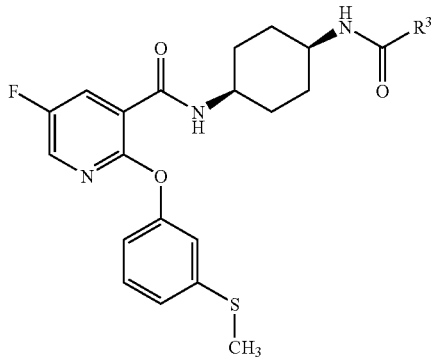

| No. | R$^3$ | Data |
|---|---|---|
| 53 | ![imidazolyl-ethyl-OTHP] | $^1$HNMR(DMSO-D$_6$, 400 MHz): 1.35(m, 4H), 1.50(m, 1H), 1.62(m, 7H), 1.76(m, 2H), 2.30(s, 3H), 3.28(m, 1H), 3.40(m, 1H), 3.55(m, 1H), 3.74(m, 2H), 3.85(m, 1H), 4.43(m, 3H), 6.92(d, 2H), 7.15(m, 2H), 7.32(t, 1H), 7.50(s, 1H), 7.90(d, 1H), 7.98(d, 1H), 8.21(d, 1H), 8.28(d, 1H). MS ES+ m/z 598 [MH]$^+$ |

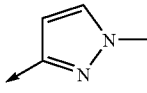

| No. | R³ | Data |
|---|---|---|
| 54 | 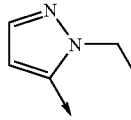 | ¹HNMR(CDCl₃, 400 MHz): 1.42–1.97(m, 14H), 2.47(s, 3H), 3.44(m, 1H), 3.60(m, 1H), 3.75(m, 1H), 4.05(m, 2H), 4.23(m, 1H), 4.34(m, 2H), 4.53(m, 1H), 6.76(m, 2H), 6.92(d, 1H), 7.03(s, 1H), 7.14(d, 1H), 7.35(t, 1H), 7.50(s, 1H), 8.00(d, 1H), 8.05(d, 1H), 8.35(d, 1H). MS ES+ m/z 620 [MNa]⁺ |
| 55 | 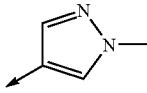 | ¹HNMR(CDCl₃, 400 MHz): 1.30–2.00(m, 14H), 2.48(s, 3H), 3.40(m, 1H), 3.53(m, 1H), 3.78(m, 1H), 4.03(m, 2H), 4.25(m, 1H), 4.50(m, 1H), 4.70(m, 2H), 6.10(d, 1H), 6.40(s, 1H), 6.90(d, 1H), 7.04(s, 1H), 7.15(d, 1H), 7.37(t, 1H), 7.49(s, 1H), 8.00(d, 1H), 8.08(d, 1H), 8.35(m, 1H). MS ES+ m/z 620 [MNa]⁺ |
| 56 | | ¹HNMR(CDCl₃, 400 MHz): 1.40–2.00(m, 14H), 2.49(s, 3H), 3.47(m, 1H), 3.67(m, 1H), 3.80(m, 1H), 4.05(m, 2H), 4.26(m, 1H), 4.35(m, 2H), 4.55(m, 1H), 5.40(m, 1H), 6.92(m, 1H), 7.05(s, 1H), 7.17(d, 1H), 7.37(t, 1H), 7.62(s, 1H), 7.90(s, 1H), 8.03(m, 1H), 8.07(s, 1H), 8.35(m, 1H). MS ES+ m/z 620 [MNa]⁺ |

Preparation 57

Syn-5-Fluoro-2-(3-methylsulfanyl-phenoxy)-N-[4-({5-methyl-1-[2-(tetrahydro-pyran-2-yloxy)-ethyl]-1H-pyrazole-3-carbonyl}-amino)-cyclohexyl]-nicotinamide

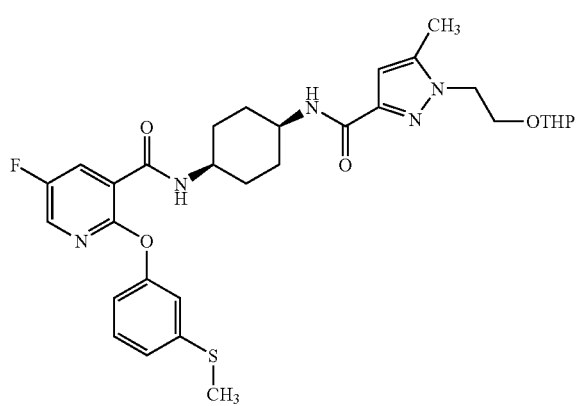

The amine of preparation 41 (200 mg, 0.47 mmol), the acid of preparation 29 (125 mg, 0.47 mmol), 1-hydroxybenzotriazole hydrate (70 mg, 0.47 mmol) and N-ethyldiisopropylamine (260 μL, 1.41 mmol) were dissolved in N,N-dimethylformamide (3 mL) and the reaction mixture treated with 1-(3-dimethylaminopropyl)-3-ethylcarbodiimide hydrochloride (140 mg, 0.71 mmol). The reaction mixture was stirred at room temperature for 18 hours and then taken up in 10% citric acid solution (50 mL) and ethyl acetate (50 mL). The organic layer was washed with 10% citric acid solution, water, saturated sodium hydrogencarbonate solution and brine. The organic layer was then dried over magnesium sulphate and concentrated in vacuo to yield the title product, 301 mg.

¹HNMR (CDCl₃, 400 MHz):1.33–1.95(m, 16H), 2.37(s, 3H), 2.48(s, 3H), 2.77(m, 1H), 3.40(m, 1H), 3.56(m, 1H), 3.76(m, 1H), 4.07(m, 2H), 4.24(m, 2H), 4.51(m, 1H), 6.52(s, 1H), 6.89(m, 1H), 7.16(m, 1H), 7.24(m, 2H), 7.39(m, 1H), 8.06(m, 1H).

MS APCI+ m/z 612 [MH]⁺

EXAMPLE 1

Syn-N-[4-(2-Hydroxy-5-hydroxymethyl-benzoylamino)-cyclohexyl]-5-methyl-2-(3-methylsulfanyl-phenoxy)-nicotinamide

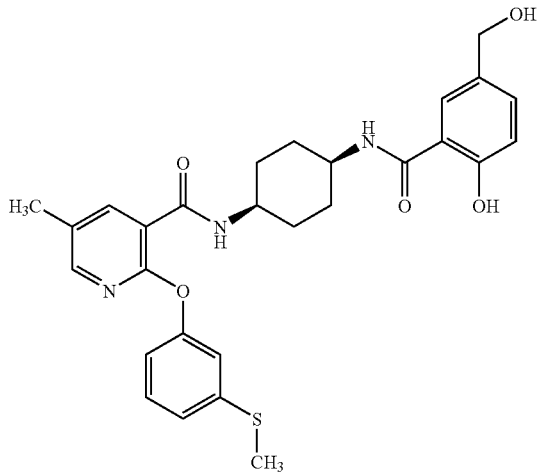

The amine of preparation 49 (100 mg, 0.26 mmol), 2-hydroxy-5-hydroxymethyl-benzoic acid (40 mg, 0.26 mmol), 1-hydroxybenzotriazole hydrate (35 mg, 0.20 mmol) and N-ethyldiisopropylamine (170 μL, 0.98 mmol) were dissolved in N,N-dimethylformamide (2 mL) and the reaction mixture treated with 1-(3-dimethylaminopropyl)-3-ethylcarbodiimide hydrochloride (74 mg, 0.38 mmol). The reaction mixture was stirred at room temperature for 18 hours. The reaction mixture was taken up in 2M hydrochloric acid (15 mL) and dichloromethane (10 mL) and the layers separated in a phase separation tube. The organic layer was washed with saturated sodium hydrogencarbonate solution, dried over magnesium sulphate and concentrated in vacuo. The residue was purified by column chromatography on silica gel eluting with pentane:ethyl acetate 80:20 to 100:0 to yield the title product 72.9 mg (54%).

$^1$HNMR (CD$_3$OD, 400 MHz): 1.72–1.89 (m, 8H), 2.37 (s, 3H), 2.42 (s, 3H), 4.01 (m, 1H), 4.13 (m, 1H), 4.53 (s, 2H), 6.86 (m, 2H), 7.04 (s, 1H), 7.11 (d, 1H), 7.32 (t, 1H), 7.38 (m, 1H), 7.79 (s, 1H), 8.03 (s, 1H), 8.09 (s, 1H).

MS ES+ m/z 544 [MNa]$^+$

EXAMPLE 2

Syn-5-Fluoro-N-[4-(2-hydroxy-4-hydroxymethyl-benzoylamino)-cyclohexyl]-2-(3-methylsulfanyl-phenoxy)-nicotinamide

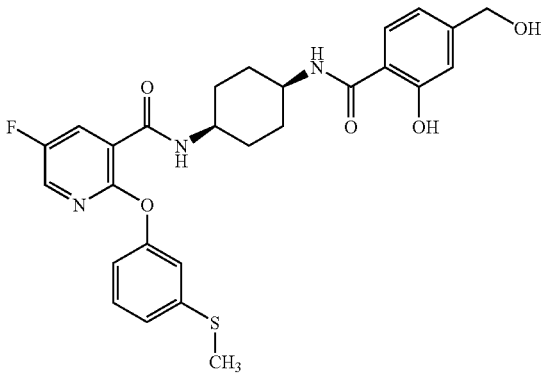

The amine of preparation 41 (600 mg, 1.47 mmol), the acid of preparation 38 (225 mg, 1.33 mmol), 1-hydroxybenzotriazole hydrate (180 mg, 1.33 mmol) and N-ethyldiisopropylamine (695 μL, 4.01 mmol) were dissolved in 1-methyl-2-pyrrolidinone (5 mL) and the reaction mixture treated with 1-(3-dimethylaminopropyl)-3-ethylcarbodiimide hydrochloride (380 mg, 2.20 mmol). The reaction mixture was stirred at room temperature for 18 hours. The reaction mixture was taken up in ethyl acetate (100 mL) and water (100 mL), the layers separated and the organics washed with 2M hydrochloric acid solution (×2), saturated sodium hydrogencarbonate solution (×2), water and brine. The organic solution was then concentrated in vacuo and the residue purified by column chromatography on silica gel eluting with pentane:ethyl acetate 80:20 to 0:100. The crude product was recrystallised from isopropyl acetate to yield the title product, 265 mg (34%).

$^1$HNMR (CD$_3$OD, 400 MHz): 1.68–1.90 (m, 8H), 2.43 (s, 3H), 4.01 (m, 1H), 4.23 (m, 1H), 4.57 (s, 2H), 6.84–6.96 (m, 3H), 7.11 (m, 2H), 7.33 (t, 1H), 7.73 (d, 1H), 8.06 (m, 1H), 8.12 (m, 1H).

MS ES+ m/z 527 [MH]$^+$

EXAMPLE 3

Syn-5-Fluoro-N-(4-{[1-(2-hydroxy-ethyl)-1H-imidazole-4-carbonyl]-amino}-cyclohexyl)-2-(3-methylsulfanyl-phenoxy)-nicotinamide

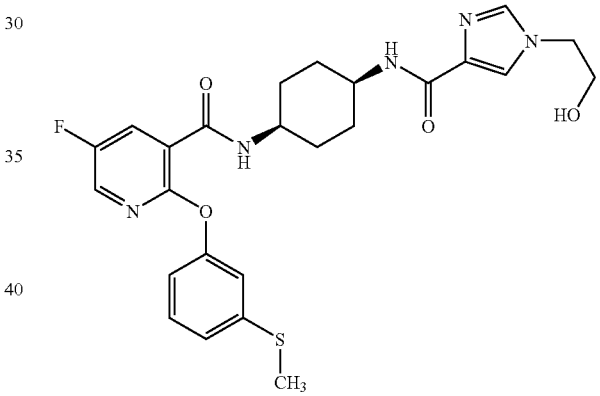

The THP protected product of preparation 52 (380 mg, 0.63 mmol) was dissolved in a mixture of acetic acid:tetrahydrofuran:water 4:2:1 (12 mL) and the reaction mixture stirred at 60° C. for 24 hours. The reaction mixture was allowed to cool and then partitioned between ethyl acetate (100 mL) and a 15% solution of potassium carbonate (200 mL). The aqueous was extracted with ethyl acetate (3×50 mL) and the organic layers were combined, dried over magnesium sulphate and concentrated in vacuo. The residue was purified by column chromatography on silica gel eluting with dichloromethane:methanol 100:1 to 50:1 to 25:1 to 15:1 to 10:1 to yield the title product, 264 mg (81%).

$^1$HNMR(DMSO-D$_6$, 400 MHz): 1.70(m, 8H), 2.45(s, 3H), 3.64(m, 2H), 3.84 m, 1H), 3.97(m, 1H), 4.03(m, 2H), 4.95(m, 1H), 6.93(m, 1H), 7.07(m, 2H), 7.25(m, 1H), 7.32 (m, 1H), 7.64(s, 2H), 8.00(m, 1H), 8.23(m, 1H), 8.30(m, 1H).

MS ES+ m/z 536 [MNa]$^+$

Microanalysis: Observed—C=57.76%, H=5.54%, N=13.37%

C$_{25}$H$_{28}$FN$_5$O$_4$S Calculated—C=58.47%, H=5.50%, N=13.64%

The following compounds, of the general formula below, were prepared by a method similar to that described for example 3 using the appropriate THP protected compound.

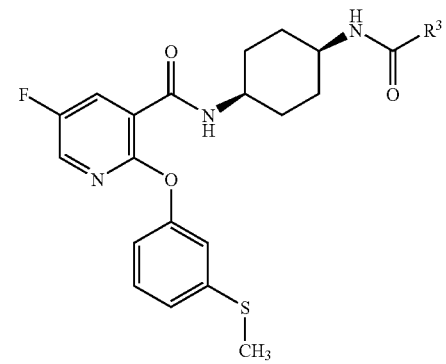

| No. | R³ | Yield % | Data |
|---|---|---|---|
| 4 | imidazolyl-CH₂CH₂-OH | 83 | ¹HNMR(DMSO-D₆, 400 MHz): 1.65(m, 6H), 1.79(m, 2H), 2.45(s 3H), 3.58(m, 2H), 3.75(m, 1H), 3.92(m, 1H), 4.27(t, 2H), 4.86(t, 1H), 6.94(d, 1H), 7.07(m, 2H), 7.30(t, 1H), 7.52(s, 1H), 7.65(s, 1H), 7.90(d, 1H), 7.98(d, 1H), 8.03(d, 1H), 8.08(d, 1H). MS ES+ m/z 536 [MNa]⁺ Microanalysis: Observed - C = 57.78%, H = 5.54%, N = 13.40% $C_{25}H_{28}FN_5O_4S$ Calculated - C = 58.47%, H = 5.50%, N = 13.64% |
| 5 | pyrazolyl-CH₂CH₂-OH | 78 | ¹HNMR(DMSO-D₆, 400 MHz): 1.65(m, 8H), 2.42(s, 3H), 3.73(m, 2H), 3.82(m, 1H), 3.97(m, 1H), 4.15(t, 2H), 4.90(t, 1H), 6.57(s, 1H), 6.92(d, 1H), 7.08(m, 2H), 7.32(t, 1H), 7.42(m, 1H), 7.74(s, 1H), 8.00(d, 1H), 8.23(m, 2H). MS ES+ m/z 536 [MNa]⁺ Microanalysis: Observed - C = 57.73%, H = 5.50%, N = 13.14% $C_{25}H_{28}FN_5O_4S$ Calculated - C = 58.47%, H = 5.50%, N = 13.64% |
| 6 | pyrazolyl-CH₂CH₂-OH | 81 | ¹HNMR(DMSO-D₆, 400 MHz): 1.60–1.85(m, 8H), 2.43(s, 3H), 3.64(m, 2H), 3.80(m, 1H), 3.93(m, 1H), 4.45(t, 2H), 4.83(t, 1H), 6.73(s, 1H), 6.92(d, 1H), 7.08(m, 2H), 7.30(t, 1H), 7.42(s, 1H), 8.00(m, 1H), 8.10(d, 1H), 8.21(s, 1H), 8.24(m, 1H). MS ES+ m/z 536 [MNa]⁺ Microanalysis: Observed - C = 57.34%, H = 5.46%, N = 13.35% $C_{25}H_{28}FN_5O_4S$ Calculated - C = 58.47%, H = 5.50%, N = 13.64% |

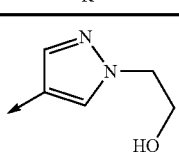

| No. | R³ | Yield % | Data |
|---|---|---|---|
| 7 | 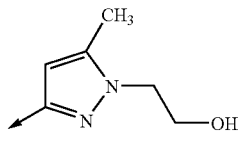 | 82 | ¹HNMR(DMSO-D₆, 400 MHz): 1.55–1.85(m, 8H), 2.43(s, 3H), 3.70(m, 2H), 3.76(m, 1H), 3.92(m, 1H), 4.13(t, 2H), 5.88(t, 1H), 6.93(d, 1H), 7.07(m, 2H), 7.32(t, 1H), 7.68(d, 1H), 7.80(s, 1H), 8.00(m, 1H), 8.13(s, 1H), 8.23(m, 2H). MS ES+ m/z 536 [MNa]⁺ Microanalysis: Observed - C = 58.23%, H = 5.49%, N = 13.52% $C_{25}H_{28}FN_5O_4S$ Calculated - C = 58.47%, H = 5.50%, N = 13.64% |
| 8 | | 77 | ¹HNMR (CDCl₃, 400 MHz): 1.56–1.94(m, 9H), 2.32(d, 3H), 2.47(s, 3H), 4.01(t, 2H), 4.08(m, 1H), 4.17(t, 2H), 4.22(m, 1H), 6.57(s, 1H), 6.75(s, 1H), 6.94(m, 1H), 7.05(m, 1H), 7.15(d, 1H), 7.37(t, 1H), 7.96(s,1H), 8.06(d, 1H), 8.35(m, 1H). MS APCl+ m/z 528 [MH]⁺ |

Example 8 was purified by column chromatography on silica gel eluting with dichloromethane:methanol:0.88 ammonia 99.5:0.5:0 to 95:5:0.5

EXAMPLE 9

Syn-5-Fluoro-2-(4-fluoro-3-methylsulfanyl-phenoxy)-N-{4-[2-(2-hydroxy-ethoxy)-benzoylamino]-cyclohexyl}-nicotinamide

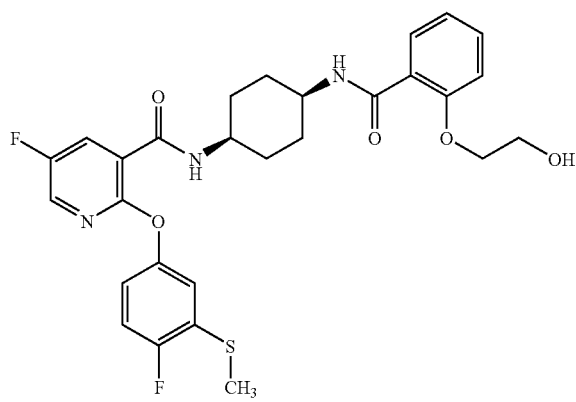

The protected alcohol of preparation 51 (215 mg, 0.34 mmol) was added to a mixture of acetic acid (4 mL), tetrahydrofuran (2 mL) and water (1 mL) and the reaction mixture stirred at 60° C. for 24 hours. The reaction mixture was concentrated in vacuo and the residue taken up in dichloromethane and washed with saturated sodium hydrogencarbonate solution (×2). The organic solution was dried over magnesium sulphate and concentrated in vacuo. The residue was recrystallised from dichloromethane, filtered and dried to yield the title product as a white solid, 84 mg (44%).

¹HNMR (DMSO-D₆, 400 MHz): 1.63–1.76 (m, 8H), 2.39 (s, 3H), 3.64 (m, 2H), 3.92 (m, 2H), 4.09 (t, 2H), 4.94 (t, 1H), 7.03 (m, 2H), 7.11–7.24 (m, 3H), 7.44 (t, 1H), 7.88 (m, 1H), 8.02 (m, 1H), 8.25 (m, 3H).

MS ES+ m/z 580 [MNa]⁺

EXAMPLE 10

Syn-5-Fluoro-N-(4-{[1-(2-hydroxy-ethyl)-5-isopropyl-1H-pyrazole-3-carbonyl]-amino}-cyclohexyl)-2-(3-methylsulfanyl-phenoxy)-nicotinamide

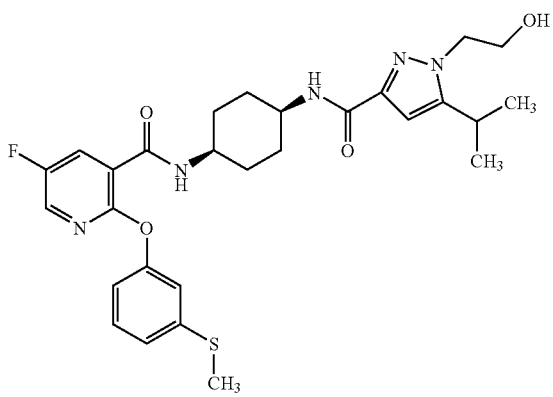

The carboxylic acid of preparation 31 (110 mg, 0.39 mmol) and N-ethyldiisopropylamine (194 mg, 1.50 mmol) were dissolved in dichloromethane (5 mL) and the solution treated with the amine of preparation 42 (185 mg, 0.45 mmol), 1-hydroxybenzotriazole hydrate (68 mg, 0.5 mmol) and lastly 1-(3-dimethylaminopropyl)-3-ethylcarbodiimide hydrochloride (115 mg, 0.6 mmol). The reaction mixture was then stirred at room temperature for 18 hours. The reaction mixture was diluted with ethyl acetate and washed with 0.2M citric acid solution, sodium hydrogencarbonate solution and brine. The organic layer was dried over magnesium sulphate and concentrated in vacuo. The residue was dissolved in acetic acid:tetrahydrofuran:water 4:2:1 and the reaction mixture stirred at room temperature for 72 hours and then at 60° C. for 24 hours. The cooled reaction mixture was diluted with ethyl acetate and washed with water, ammonium hydroxide solution and brine. The organic layer was dried over magnesium sulphate and concentrated in vacuo. The residue was purified by column chromatography on silica gel eluting with ethyl acetate and the crude product crystallised from ether to yield the title product, 71 mg (33%).

$^1$HNMR(CDCl$_3$, 400 MHz): 1.26(d, 6H), 1.60(m, 2H), 1.87(m, 7H), 2.47(s, 3H), 2.97(m, 1H), 4.03(t, 2H), 4.08(m, 1H), 4.19(m, 3H), 6.62(s, 1H), 6.71(d, 1H), 6.93(dd, 1H), 7.05(s, 1H), 7.15(d, 1H), 7.37(t, 1H), 7.99(d, 1H), 8.06(d, 1H), 8.35(dd, 1H).

MS APCI+ m/z 446 [MH]$^+$

Microanalysis: Observed—C=60.46%, H=6.20%, N=12.45%

C$_{28}$H$_{34}$FN$_5$O$_4$S Calculated—C=60.52%, H=6.17%, N=12.60%

The following compounds, of the general formula below, were prepared by a method similar to that described in example 13 using the appropriate amines and carboxylic acids:

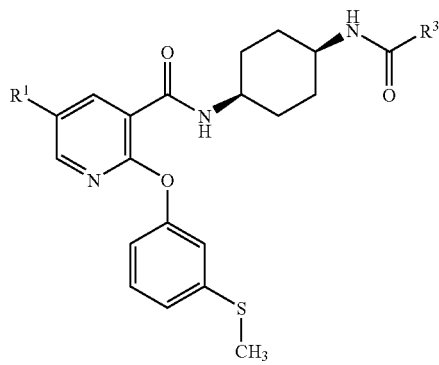

| No. | R$^1$ | R$^3$ | Yield % | Data |
|---|---|---|---|---|
| 11 | F | H$_3$C-... -O-CH$_2$CH$_2$OH | 66 | $^1$HNMR (CDCl$_3$, 400 MHz): 1.62–1.94(m, 8H), 2.34(s, 3H), 2.42(s, 3H), 3.71(m, 2H), 4.08(m, 2H), 4.21(m, 2H), 6.80(d, 1H), 6.92(m, 1H), 7.07(m, 1H), 7.16(m, 2H), 7.37(m, 1H), 7.92(m, 1H), 8.05(m, 3H), 8.35(m, 1H). MS ES+ m/z 576 [MNa]$^+$ |

-continued

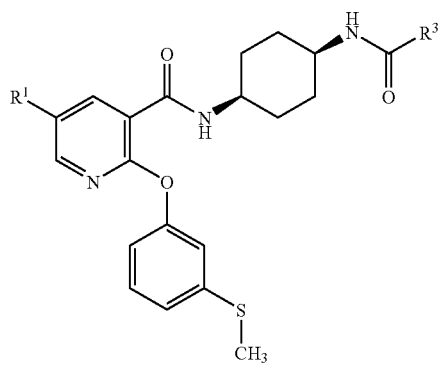

| No. | R¹ | R³ | Yield % | Data |
|---|---|---|---|---|
| 12 | F | 5-methyl-2-(2-hydroxyethoxy)phenyl (H₃C at 5, OCH₂CH₂OH at 2) | 43 | ¹HNMR (CDCl₃, 400 MHz): 1.62–1.94(m, 8H), 2.34(s, 3H), 2.42(s, 3H), 3.71(m, 2H), 4.08(m, 2H), 4.21(m, 2H), 6.64(m, 1H), 6.85(d, 1H), 6.92(d, 1H), 7.03(m, 1H), 7.17(m, 1H), 7.37(m, 1H), 8.04(m, 4H), 8.38(m, 1H). MS ES+ m/z 576 [MNa]⁺ |
| 13 | F | 2,6-disubstituted (CH₃, OCH₂CH₂OH) phenyl | 43 | ¹HNMR (CDCl₃, 400 MHz): 1.62–1.94(m, 8H), 2.34(s, 3H), 2.42(s, 3H), 3.71(m, 2H), 4.08(m, 2H), 4.21(m, 2H), 6.88(d, 1H), 7.10(m, 3H), 7.23(m, 1H), 7.34(m, 1H), 7.41(m, 1H), 7.68(m, 1H), 8.00(m, 2H), 8.32(d, 1H). MS ES+ m/z 576 [MNa]⁺ |
| 14 | F | 4-chloro-2-(2-hydroxyethoxy)phenyl | 21 | ¹HNMR (CDCl₃, 400 MHz): 1.60–2.00(m, 8H), 2.46(s, 3H), 3.76(t, 2H), 4.10(t, 2H), 4.12–4.30(m, 2H), 6.82(d, 1H), 6.92(m, 1H), 7.06(s, 1H), 7.16(d, 1H), 7.32(m, 2H), 8.02(m, 3H), 8.10(d, 1H), 8.34(m, 1H). MS ES m/z 596 [MNa]⁺ |
| 15 | F | 5-chloro-2-(2-hydroxyethoxy)phenyl | 63 | ¹HNMR (CDCl₃, 400 MHz): 1.60–1.90(m, 8H), 2.46(s, 3H), 3.74(m, 2H), 4.04–4.26(m, 4H), 6.86(d, 1H), 6.92(m, 1H), 6.98(m, 1H), 7.06(m, 1H), 7.12(d, 1H), 7.34(t, 1H), 8.02(m, 4H), 8.28(m, 1H). MS ES+ m/z 596 [MNa]⁺ |
| 16 | F | 2-chloro-6-(2-hydroxyethoxy)phenyl | 28 | ¹HNMR (CDCl₃, 400 MHz): 1.52–1.96(m, 8H), 2.44(s, 3H), 3.78(m, 2H), 4.10(m, 3H), 4.22(m, 1H), 6.92(m, 1H), 7.06(m, 1H), 7.14(m, 2H), 7.34(t, 1H), 7.48(2H, m), 7.84(m, 1H), 8.02(m, 2H), 8.32(m, 1H). MS ES+ m/z 596 [MNa]⁺ |

-continued

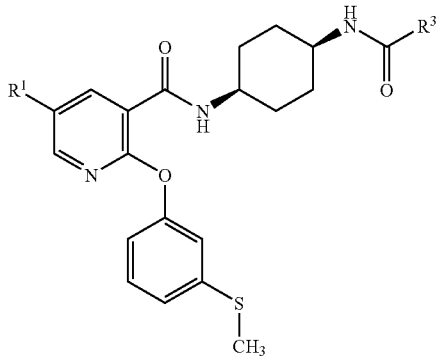

| No. | R¹ | R³ | Yield % | Data |
|---|---|---|---|---|
| 17 | F | pyrazole-CH₃ with N-CH₂CH₂OH | 56 | ¹HNMR (CD₃OD, 400 MHz): 1.27(t, 3H), 1.64–1.92(m, 8H), 2.42(s, 3H), 2.72(q, 2H), 3.87(t, 2H), 3.97(m, 1H), 4.13 (m, 1H), 4.18(t, 2H), 6.50 (s, 1H), 6.91(m, 2H), 7.11 (m, 1H), 7.33(t, 3H), 8.07 (m, 1H), 8.11(m, 1H). MS APCI+ m/z 542 [MH]⁺ |
| 18 | Cl | 2-methylphenoxy-CH₂CH₂OH | 82 | MS ES+ m/z 556 [MH]⁺ |

Example 11 was purified by column chromatography on silica gel eluting with dichloromethane:methanol 99.5: 0.5 to 95:5.

Examples 12 and 13 were purified by column chromatography on silica gel eluting with dichloromethane: acetonitrile 80:20 to 0:100.

Example 17 was prepared using triethylamine.

In Vitro Activity of the Nicotinamide Derivatives

The PDE4 inhibitory activity of the nicotinamide derivatives of the formula (1) is determined by the ability of compounds to inhibit the hydrolysis of cAMP to AMP by PDE4 (see also reference 1). Tritium labelled cAMP is incubated with PDE4. Following incubation, the radiolabelled AMP produced is able to bind yttrium silicate SPA beads. These SPA beads subsequently produce light that can be quantified by scintillation counting. The addition of a PDE4 inhibitor prevents the formation of AMP from cAMP and counts are diminished. The $IC_{50}$ of a PDE4 inhibitor can be defined as the concentration of a compound that leads to a 50% reduction in counts compared to the PDE4 only (no inhibitor) control wells.

The anti-inflammatory properties of the nicotinamide derivatives of the formula (1) are demonstrated by their ability to inhibit TNFα release from human peripheral blood mononuclear cells (see also reference 2). Venous blood is collected from healthy volunteers and the mononuclear cells purified by centrifugation through Histopaque (Ficoll) cushions. TNFα production from these cells is stimulated by addition of lipopolysaccharide. After 18 hours incubation in the presence of LPS, the cell supernatant is removed and the concentration of TNFα in the supernatant determined by ELISA. Addition of PDE4 inhibitors reduces the amount of TNFα produced. An $IC_{50}$ is determined which is equal to the concentration of compound that gives 50% inhibition of TNFα production as compared to the LPS stimulated control wells.

All the examples were tested in the assay described above and found to have an $IC_{50}$ (TNFα screen) of less than 30 nM. And for most of the tested compounds, they were found to have an $IC_{50}$ (TNFα screen) of even less than 10 nM.

For illustrating purpose, the following table indicates the exact $IC_{50}$ (TNFα screen) of some representative examples of the present invention which have an $IC_{50}$ (TNFα screen) of even less than 5 nM:

| Example N° | $IC_{50}$ (nM) |
|---|---|
| 2 | 0.6 |
| 3 | 1.6 |
| 5 | 0.24 |
| 7 | 4.6 |
| 8 | 0.2 |
| 9 | 0.36 |
| 10 | 2.5 |
| 11 | 0.8 |
| 12 | 0.3 |
| 13 | 0.07 |
| 14 | 0.6 |
| 15 | 1.6 |
| 16 | 1.0 |
| 17 | 0.05 |
| 18 | 0.15 |

References

1. Thompson J W, Teraski W L, Epstein P M, Strada S J., "Assay of nucleotidephosphodiesterase and resolution of multiple molecular forms of the isoenzyme", *Advances in cyclic nucleotides research*, edited by Brooker G, Greengard P, Robinson G A. Raven Press, New York 1979, 10, p. 69–92.
2. Yoshimura T, Kurita C, Nagao T, Usami E, Nakao T, Watanabe S, Kobayashi J, Yamazaki F, Tanaka H, Nagai H., "Effects of cAMP-phosphodiesterase isozyme inhibitor on cytokine production by lipopolysaccharide-stimulated human peripheral blood mononuclear cells", *Gen. Pharmacol.*, 1997, 29(4), p. 63

The invention claimed is:

1. A compound of formula (I):

or a pharmaceutically acceptable salt or solvate thereof, wherein:

$R^1$ and $R^2$ are each independently hydrogen, halo or $(C_1-C_3)$alkyl; and $R^3$ is a C-linked 5- or 6-membered heteroaryl incorporating one to three nitrogen atoms, said heteroaryl being substituted by hydroxy$(C_1-C_4)$alkyl and said heteroaryl optionally being further substituted independently by one to three hydroxy, halo, $(C_1-C_4)$alkyl or $(C_1-C_4)$alkoxy; or phenyl substituted by hydroxy$(C_1-C_4)$alkyl or hydroxy$(C_2-C_4)$alkoxy and said phenyl optionally being further substituted independently by one to three hydroxy, hydroxy$(C_1-C_3)$alkyl, $(C_1-C_4)$alkoxy, $(C_1-C_4)$alkyl or halo.

2. A compound of claim 1, or a pharmaceutically acceptable salt thereof, wherein $R^1$ is H, F, Cl or methyl.

3. A compound of claim 2, or a pharmaceutically acceptable salt thereof, wherein $R^1$ is F, Cl or methyl.

4. A compound of claim 3, or a pharmaceutically acceptable salt thereof, wherein $R^2$ is H or F.

5. A compound of claim 4, or a pharmaceutically acceptable salt thereof, wherein $R^2$ is H.

6. A compound of claim 5, or a pharmaceutically acceptable salt thereof, wherein $R^3$ is a C-linked 5-membered aromatic heteroaryl containing 2 or 3 nitrogen atoms, said heteroaryl being substituted by hydroxy$(C_1-C_4)$alkyl and said heteroaryl optionally being further substituted independently by one to three hydroxy, halo, $(C_1-C_4)$alkyl or $(C_1-C_4)$alkoxy; or phenyl substituted by hydroxy$(C_1-C_4)$alkyl or hydroxy$(C_2-C_4)$alkoxy.

7. A compound of claim 6, or a pharmaceutically acceptable salt thereof, wherein $R^3$ is a C-linked pyrazolyl or imidazolyl, said pyrazolyl and imidazolyl being substituted by hydroxy$(C_1-C_4)$alkyl and said heteroaryl optionally being further substituted independently by one to three hydroxy, halo, $(C_1-C_4)$alkyl or $(C_1-C_4)$alkoxy; or phenyl substituted by hydroxy$(C_1-C_4)$alkyl or hydroxy$(C_2-C_4)$alkoxy.

8. A compound of claim 1, or a pharmaceutically acceptable salt thereof, wherein $R^3$ is a C-linked pyrazolyl or imidazolyl wherein one of the ring nitrogen atoms is substituted by hydroxy$(C_2-C_3)$alkyl and the ring is optionally further substituted independently by one to three $(C_1-C_4)$alkyl or $(C_1-C_4)$alkoxy.

9. A compound of claim 8, or a pharmaceutically acceptable salt thereof, wherein $R^3$ is a C-linked pyrazolyl or imidazolyl wherein one of the ring nitrogen atoms is substituted by hydroxy$(C_2-C_3)$alkyl and the ring is optionally further substituted independently by one to three $(C_1-C_4)$alkyl.

10. A compound of claim 7, or a pharmaceutically acceptable salt thereof, wherein one of the ring nitrogen atoms in said pyrazolyl or imidazolyl is substituted by hydroxyethyl or hydroxypropyl.

11. A compound of claim 7, or a pharmaceutically acceptable salt thereof, wherein one of the ring nitrogen atoms of said pyrazolyl or imidazolyl is substituted by hydroxyethyl or hydroxypropyl and said ring is further optionally substituted independently by one to three methyl, ethyl, n-propyl or isopropyl.

12. A compound of claim 7, or a pharmaceutically acceptable salt thereof, wherein one of the ring nitrogen atoms of said pyrazolyl or imidazolyl is substituted by hydroxyethyl or hydroxypropyl and said ring is further substituted at the 5-position by methyl, ethyl, n-propyl or isopropyl.

13. A compound of claim 1, or a pharmaceutically acceptable salt thereof, wherein $R^3$ is phenyl substituted by hydroxymethyl or hydroxyethoxy and said phenyl is optionally further substituted independently by one to three hydroxy, methyl, ethyl, F or Cl.

14. A compound of claim 13, or a pharmaceutically acceptable salt thereof, wherein $R^3$ is phenyl substituted by hydroxyethoxy and said phenyl is optionally further substituted independently by one to three methyl or Cl.

15. A compound of claim 14, or a pharmaceutically acceptable salt thereof, wherein $R^3$ is phenyl substituted at the 2-position by a hydroxyethoxy group.

16. A compound of claim 1 wherein $R^3$ is phenyl substituted at the 2-position by hydroxy$(C_2-C_3)$alkoxy and said phenyl is further substituted at the 4-position by hydroxy, $(C_1-C_3)$alkoxy, $(C_1-C_3)$alkyl or halo.

17. A compound of claim 1, or a pharmaceutically acceptable salt thereof, wherein $R^3$ is phenyl substituted by hydroxy$(C_1-C_3)$alkyl and said phenyl is optionally further substituted independently by one to three hydroxy, $(C_1-C_3)$alkoxy, $(C_1-C_3)$alkyl or halo.

18. A compound of claim 17, or a pharmaceutically acceptable salt thereof, wherein $R^3$ is phenyl substituted by hydroxy$(C_1-C_3)$alkyl and said phenyl is optionally further substituted independently by one to three hydroxy, methyl, ethyl, hydroxyethyl, hydroxymethyl, F or Cl.

19. A compound of claim 18, or a pharmaceutically acceptable salt thereof, wherein $R^3$ is phenyl substituted at the 3- or 4-position by hydroxy$(C_1-C_3)$alkyl and said phenyl is optionally further substituted independently by one to three hydroxy, methyl, ethyl, F or Cl.

20. A compound of claim 19, or a pharmaceutically acceptable salt thereof, wherein $R^3$ is phenyl substituted at the 3- or 4-position by hydroxymethyl and said phenyl is optionally further substituted at the 2-position by hydroxy.

21. A compound of claim 1, or a pharmaceutically acceptable salt thereof, wherein $R^1$ is F, Cl or methyl; $R^2$ is H or F; and $R^3$ is an optionally substituted C-linked pyrazolyl or imidazolyl.

22. A compound of claim 1, or a pharmaceutically acceptable salt thereof, wherein $R^1$ is F, Cl or methyl; $R^2$ is H or F; and $R^3$ is phenyl substituted by hydroxy($C_1$–$C_3$)alkyl or hydroxy($C_2$–$C_3$)alkoxy and said phenyl is optionally further substituted independently by one to three hydroxy, ($C_1$–$C_3$) alkoxy, ($C_1$–$C_3$)alkyl or halo.

23. Syn-N-[4-(2-Hydroxy-5-hydroxymethyl-benzoylamino)-cyclohexyl]-5-methyl-2-(3-methylsulfanyl-phenoxy)-nicotinamide;

Syn-5-Fluoro-N-[4-(2-hydroxy-4-hydroxymethyl-benzoylamino)-cyclohexyl]-2-(3-methylsulfanyl-phenoxy)-nicotinamide;

Syn-5-Fluoro-N-(4-{[1-(2-hydroxy-ethyl)-1H-imidazole-4-carbonyl]-amino}-cyclohexyl)-2-(3-methylsulfanyl-phenoxy)-nicotinamide;

Syn-5-Fluoro-N-(4-{[3-(2-hydroxy-ethyl)-3H-imidazole-4-carbonyl]-amino}-cyclohexyl)-2-(3-methylsulfanyl-phenoxy)-nicotinamide;

Syn-5-Fluoro-N-(4-{[1-(2-hydroxy-ethyl)-1H-pyrazole-3-carbonyl]-amino}-cyclohexyl)-2-(3-methylsulfanyl-phenoxy)-nicotinamide;

Syn-5-Fluoro-N-(4-{[2-(2-hydroxy-ethyl)-2H-pyrazole-3-carbonyl]-amino}-cyclohexyl)-2-(3-methylsulfanyl-phenoxy)-nicotinamide;

Syn-5-Fluoro-N-(4-{[1-(2-hydroxy-ethyl)-1H-pyrazole-4-carbonyl]-amino}-cyclohexyl)-2-(3-methylsulfanyl-phenoxy)-nicotinamide;

Syn-5-Fluoro-N-(4-{[1-(2-hydroxy-ethyl)-5-methyl-1H-pyrazole-3-carbonyl]-amino}-cyclohexyl)-2-(3-methylsulfanyl-phenoxy)-nicotinamide;

Syn-5-Fluoro-2-(4-fluoro-3-methylsulfanyl-phenoxy)-N-{4-[2-(2-hydroxy-ethoxy)-benzoylamino]-cyclohexyl}-nicotinamide;

Syn-5-Fluoro-N-(4-{[1-(2-hydroxy-ethyl)-5-isopropyl-1H-pyrazole-3-carbonyl]-amino}-cyclohexyl)-2-(3-methylsulfanyl-phenoxy)-nicotinamide;

Syn-5-Fluoro-N-{4-[2-(2-hydroxy-ethoxy)-5-methyl-benzoylamino]-cyclohexyl}-2-(3-methylsulfanyl-phenoxy)-nicotinamide;

Syn-5-Fluoro-N-{4-[2-(2-hydroxy-ethoxy)-4-methyl-benzoylamino]-cyclohexyl}-2-(3-methylsulfanyl-phenoxy)-nicotinamide;

Syn-5-Fluoro-N-{4-[2-(2-hydroxy-ethoxy)-3-methyl-benzoylamino]-cyclohexyl}-2-(3-methylsulfanyl-phenoxy)-nicotinamide;

Syn-N-{4-[5-Chloro-2-(2-hydroxy-ethoxy)-benzoylamino]-cyclohexyl}-5-fluoro-2-(3-methylsulfanyl-phenoxy)-nicotinamide;

Syn-N-{4-[4-Chloro-2-(2-hydroxy-ethoxy)-benzoylamino]-cyclohexyl}-5-fluoro-2-(3-methylsulfanyl-phenoxy)-nicotinamide;

Syn-N-{4-[3-Chloro-2-(2-hydroxy-ethoxy)-benzoylamino]-cyclohexyl}-5-fluoro-2-(3-methylsulfanyl-phenoxy)-nicotinamide;

Syn-N-(4-{[5-Ethyl-1-(2-hydroxy-ethyl)-1H-pyrazole-3-carbonyl]-amino}-cyclohexyl)-5-fluoro-2-(3-methylsulfanyl-phenoxy)-nicotinamide; or Syn-5-Chloro-N-{4-[2-(2-hydroxy-ethoxy)-benzoylamino]-cyclohexyl}-2-(3-methylsulfanyl-phenoxy)-nicotinamide;

or a pharmaceutically acceptable salt or solvate thereof.

24. A pharmaceutical composition comprising a compound of claim 1 or a pharmaceutically acceptable salt or solvate thereof and a pharmaceutically acceptable excipient, diluent or carrier.

25. A method of treating a disease, disorder or condition in a mammal, which method comprises administering to said mammal in need of such treatment a therapeutically effective amount of a compound of claim 1, a pharmaceutically acceptable salt thereof or a pharmaceutical composition comprising a compound of claim 1 or a pharmaceutically acceptable salt thereof and a pharmaceutically acceptable carrier, diluent or excipient, wherein the disease, disorder or condition is selected from:

atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma and wheezy infant syndrome, chronic or acute bronchoconstriction, chronic bronchitis, small airways obstruction, and emphysema, chronic eosinophilic pneumonia, chronic obstructive pulmonary disease (COPD), COPD that includes chronic bronchitis, pulmonary emphysema or dyspnea associated therewith, COPD that is characterized by irreversible, progressive airways obstruction, adult respiratory distress syndrome (ARDS) and exacerbation of airways hyper-reactivity consequent to other drug therapy, aluminosis or bauxite workers' disease, anthracosis or miners' asthma, asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma and talc pneumoconiosis, acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, cylindric bronchiectasis, sacculated bronchiectasis, fusiform bronchiectasis, capillary bronchiectasis, cystic bronchiectasis, dry bronchiectasis and follicular bronchiectasis, and seasonal allergic rhinitis, perennial allergic rhinitis, purulent or nonpurulent sinusitis, acute or chronic sinusitis and ethmoid, frontal, maxillary, or sphenoid sinusitis.

26. A method of claim 25 wherein the disease, disorder or condition is chronic obstructive pulmonary disease, asthma or chronic bronchitis.

* * * * *